United States Patent
Yamashita et al.

(10) Patent No.: US 7,241,608 B2
(45) Date of Patent: Jul. 10, 2007

(54) CAT KIDNEY DISEASE MARKER

(75) Inventors: Tetsuro Yamashita, Morioka (JP); Masao Miyazaki, Morioka (JP)

(73) Assignee: Tohoku Techno Arch Co., Ltd. (JP)

( * ) Notice: Subject to any disclaimer, the term of this patent is extended or adjusted under 35 U.S.C. 154(b) by 0 days.

(21) Appl. No.: 11/227,614

(22) Filed: Sep. 15, 2005

(65) Prior Publication Data

US 2006/0094863 A1    May 4, 2006

Related U.S. Application Data

(62) Division of application No. 10/233,933, filed on Sep. 3, 2002, now Pat. No. 7,026,151.

(30) Foreign Application Priority Data

Apr. 3, 2002   (JP)  ............................. 2002-057908

(51) Int. Cl.
- *C12N 9/16* (2006.01)
- *C12N 1/20* (2006.01)
- *C12N 15/00* (2006.01)
- *C12Q 1/44* (2006.01)
- *C07H 21/04* (2006.01)

(52) U.S. Cl. ................... 435/196; 435/19; 435/252.3; 435/320.1; 536/23.2

(58) Field of Classification Search ................ 435/196, 435/183, 252.3, 320.1; 536/23.2
See application file for complete search history.

(56) References Cited

U.S. PATENT DOCUMENTS 6,664,091 B2 * 12/2003 Curtis et al. ................. 435/197
6,783,969 B1 * 8/2004 Tang et al. ................... 435/219
6,914,047 B2 * 7/2005 Ruben et al. .................. 514/12
6,924,099 B1 * 8/2005 Bunch et al. .................... 435/6
6,974,667 B2 * 12/2005 Horne et al. .................... 435/6

FOREIGN PATENT DOCUMENTS

JP      09-171019     6/1994
JP      10-132817     5/1998

OTHER PUBLICATIONS

Miyazaki, J., et al. (2003) Biochem. J. 370, 101-110.*
Sequence searches, U.S. Appl. No. 11/227,614.*
"Rat Kidney Carboxylesterase" *The Journal of Biological Chemistry* vol. 269, No. 47, Issue of Nov. 25, pp. 29688-29696, 1994 Yan et al.
Pamphlet of The Molecular Biology Society of Japan annual meeting 2001 (front page, p. 206 and p. 795).

* cited by examiner

*Primary Examiner*—Tekchand Saidha
(74) *Attorney, Agent, or Firm*—Hayes Soloway P.C.

(57) ABSTRACT

In view of the increase in the number of cases with nephropathy in aged animals of the cat family, the invention provides a marker for early diagnosis of feline nephropathy which can substitute for the conventional complicated methods of diagnosing nephropathy such as blood examination, kidney radiography using a contrast medium, and ultrasonic image analysis. It was found that cats with nephropathy show markedly lowered levels of excretion of a novel protein (named cauxin) with a molecular weight of 70 K, which is excreted into urine in high concentrations in normal adult cats showing no clinical abnormality. When the protein is used as a marker in diagnosing feline nephropathy, feline nephropathy can be detected in a simple and exact manner.

7 Claims, 17 Drawing Sheets

Fig. 4

```
Cauxin   IRFVFGGAFLKGDIVMFEGATEEEKLLSRKMMRYWANFARTGDPNGEGVPLWPAYTQSEQYLKLDLSVSVGQKLKEQEVEFWMNTIVP
Rat K    LYS...API.────RD..S...IK..KMV.KF.......N.N...R.L.H..Q.D.K.E..QIGATTQQS.R..AE..A..TQLLAK────RQ.QPHHNEL
Rat L    VYS...API.────RD..S...IK..KMV.KF.......N.N...AR.L.H..Q.D.K.E..QIGATTQQS.R..AE..A..TQLLAK────RQ.QPHHNEL
Pig      .FS...FPL.────KGD.P...VS..KTV.KF.......S.N......L.H..M.D.E.G..QIGVNTQAAKR..GE..A..NDLLSKEAAKKP.KIKHAEL
Human    LFS...AP..────K...S...IR..KMV.KF.......N.N.....L.H..E.N.K.G..QIGANTQAA...DK..A..TNLFAKKAVEKP.QTEHIEL
```

C-terminal amino acid sequence alignment of cauxin, carboxyl esterase from rat kidney, rat liver, pig liver and human liver.

Fig. 9
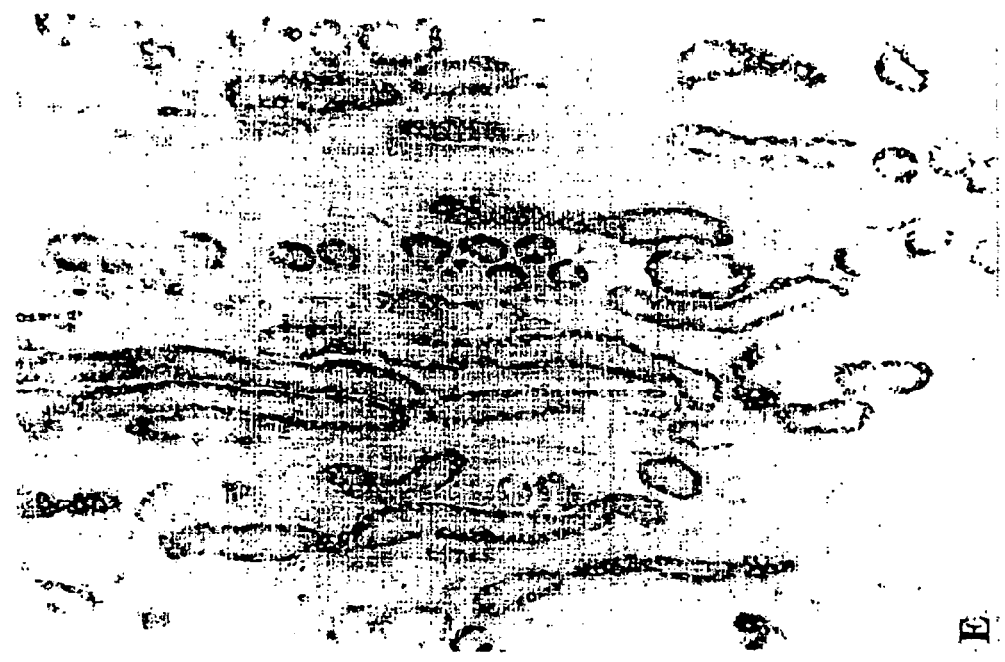
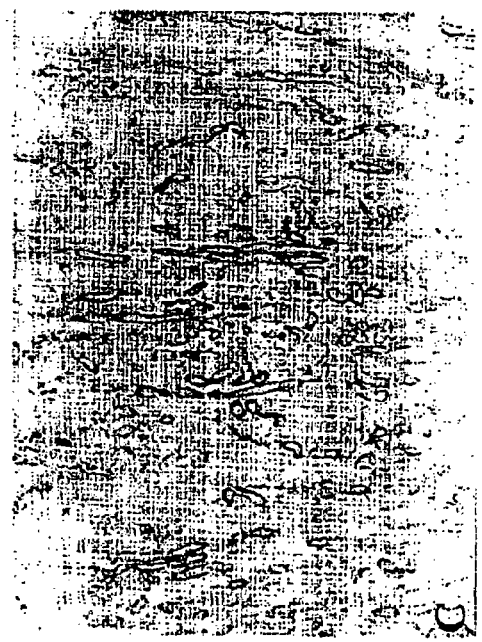
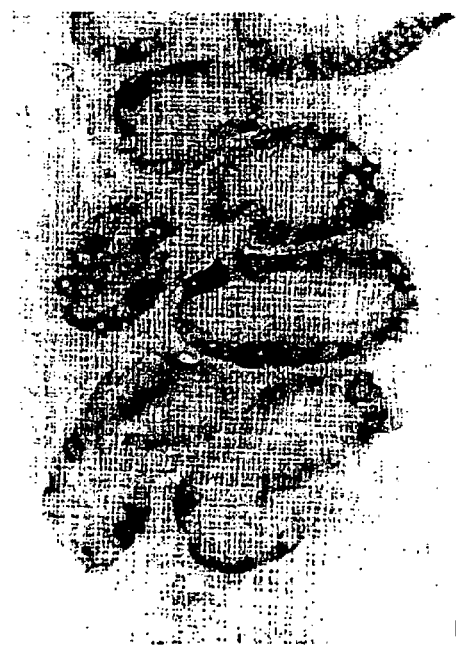

Kidney tissue (stained with H & E, x 200) of a cat with interstitial nephritis

Kidney of a normal adult cat

Kidney of a cat with terminal nephropathy

SEQUENCE LISTING

<160> NUMBER OF SEQ ID NOS: 4

<210> SEQ ID NO 1
<211> LENGTH: 1629
<212> TYPE: DNA
<213> ORGANISM: Felis catus

<400> SEQUENCE: 1

| | | | | | |
|---|---|---|---|---|---|
| atgtgggtgc | acccaggccg | gaccctgatc | tgggctcttt | gggtccttgc | agctgtcatt | 60 |
| aaggggccag | ctgctgatgc | accagtgagg | agcaccaggc | tgggatgggt | ccggggggaag | 120 |
| caaaccactg | tactgggaag | caccgtgcct | gtgaacatgt | tcctcgggat | cccctatgct | 180 |
| gcacctcctc | tagggcccct | gcgatttaag | caaccaaagc | tgctctgcc | cgggaatgac | 240 |
| ttccgaaatg | ccacatccta | ccctaaatta | tgcttccagg | acttagagtg | gctggtctcc | 300 |
| tatcaacacg | ttctcaaagt | gcgttacccc | aaattggaag | cgtccgaaga | ctgcctgtac | 360 |
| cttaacatct | atgcgccagc | ccatgcggac | aatggctcca | acctccctgt | catggtgtgg | 420 |
| ttccccgggg | gtgccttcaa | gatgggctca | gcttcctcct | tcgatgggtc | cgccttggct | 480 |
| gcctacgagg | acgtgctgat | cgtgactacc | cagtaccggc | taggaatatt | tggttttttc | 540 |
| gacacagggg | atgagcatgc | ccgggggaac | tgggccttgc | tggaccaggt | ggctgcccta | 600 |
| acctgggtcc | gggacaacat | cgagttcttc | ggtggtgacc | cacgctccgt | gaccatcttt | 660 |
| ggagagtcag | cgggagccat | cagtgtttcc | agcctcattc | tgtcccccat | agccaatggc | 720 |
| ttattccaca | aagccatcat | ggagagtggg | gtggccatcc | tgcctttact | gatgagaccc | 780 |
| cctggtgatg | agaggaagaa | ggatttgcag | gtgcttgcgc | gtatctgtgg | ttgccatgcg | 840 |
| tctgactctg | ctgccctgct | gcagtgcctg | agggcaaaac | cctccgagga | gttgatggac | 900 |
| atcagcaaga | aactcacgtt | ttccattcca | gtgattgatg | acttttttctt | tcctgatgag | 960 |
| cctgtagccc | tattgactca | aaaagcattt | aattcagttc | cttctatcat | cggagtcaat | 1020 |
| aaccacgagt | gtgccttcct | tctgtccacg | gagttttctg | agatcctcgg | gggctccaac | 1080 |
| aggtctctgg | ccctctactt | agtacacacg | ttcctgaata | ttcccaccca | gtatttgcac | 1140 |
| cttgtggctg | atcattactt | ctacaacaag | cactcccccgg | ttgaaatacg | agatagtttt | 1200 |
| ctggacttgc | ttggagatgt | gctctttgtg | gtccctgggg | tggtcacagc | tcgatatcat | 1260 |
| agagatgctg | gtgcacctgt | ctacttctat | gagtttcaac | acccgcccca | gtgcttaaac | 1320 |
| gacacgaggc | cagctttcgt | gaaagccgat | cactctgatg | aaatccgctt | cgtctttgga | 1380 |
| ggtgccttcc | tgaaaggcga | cattgtcatg | ttcgaaggag | ccaccgagga | ggagaaattg | 1440 |
| ctgagcagga | agatgatgag | gtactgggcc | aactttgctc | ggaccgggga | ccctaacggg | 1500 |
| gaaggtgtgc | ctctgtggcc | agcctacacc | cagagcgagc | agtacctgaa | gctggatttg | 1560 |
| agtgtgagcg | tgggacagaa | actgaaggag | caagaggtgg | agttttggat | gaataccatt | 1620 |
| gtcccctga | | | | | 1629 |

<210> SEQ ID NO 2
<211> LENGTH: 542
<212> TYPE: PRT
<213> ORGANISM: Felis catus

<400> SEQUENCE: 2

Met Trp Val His Pro Gly Arg Thr Leu Ile Trp Ala Leu Trp Val Leu
1               5                   10                  15

-continued

```
Ala Ala Val Ile Lys Gly Pro Ala Ala Asp Ala Pro Val Arg Ser Thr
             20                  25                  30
Arg Leu Gly Trp Val Arg Gly Lys Gln Thr Thr Val Leu Gly Ser Thr
             35                  40                  45
Val Pro Val Asn Met Phe Leu Gly Ile Pro Tyr Ala Ala Pro Pro Leu
 50                  55                  60
Gly Pro Leu Arg Phe Lys Gln Pro Lys Pro Ala Leu Pro Gly Asn Asp
 65                  70                  75                  80
Phe Arg Asn Ala Thr Ser Tyr Pro Lys Leu Cys Phe Gln Asp Leu Glu
                 85                  90                  95
Trp Leu Val Ser Tyr Gln His Val Leu Lys Val Arg Tyr Pro Lys Leu
             100                 105                 110
Glu Ala Ser Glu Asp Cys Leu Tyr Leu Asn Ile Tyr Ala Pro Ala His
             115                 120                 125
Ala Asp Asn Gly Ser Asn Leu Pro Val Met Val Trp Phe Pro Gly Gly
130                 135                 140
Ala Phe Lys Met Gly Ser Ala Ser Ser Phe Asp Gly Ser Ala Leu Ala
145                 150                 155                 160
Ala Tyr Glu Asp Val Leu Ile Val Thr Thr Gln Tyr Arg Leu Gly Ile
                 165                 170                 175
Phe Gly Phe Phe Asp Thr Gly Asp Glu His Ala Arg Gly Asn Trp Ala
             180                 185                 190
Leu Leu Asp Gln Val Ala Ala Leu Thr Trp Val Arg Asp Asn Ile Glu
             195                 200                 205
Phe Phe Gly Gly Asp Pro Arg Ser Val Thr Ile Phe Gly Glu Ser Ala
210                 215                 220
Gly Ala Ile Ser Val Ser Ser Leu Ile Leu Ser Pro Ile Ala Asn Gly
225                 230                 235                 240
Leu Phe His Lys Ala Ile Met Glu Ser Gly Val Ala Ile Leu Pro Leu
                 245                 250                 255
Leu Met Arg Pro Pro Gly Asp Glu Arg Lys Lys Asp Leu Gln Val Leu
             260                 265                 270
Ala Arg Ile Cys Gly Cys His Ala Ser Asp Ser Ala Ala Leu Leu Gln
             275                 280                 285
Cys Leu Arg Ala Lys Pro Ser Glu Glu Leu Met Asp Ile Ser Lys Lys
290                 295                 300
Leu Thr Phe Ser Ile Pro Val Ile Asp Asp Phe Phe Pro Asp Glu
305                 310                 315                 320
Pro Val Ala Leu Leu Thr Gln Lys Ala Phe Asn Ser Val Pro Ser Ile
                 325                 330                 335
Ile Gly Val Asn Asn His Glu Cys Ala Phe Leu Leu Ser Thr Glu Phe
             340                 345                 350
Ser Glu Ile Leu Gly Gly Ser Asn Arg Ser Leu Ala Leu Tyr Leu Val
             355                 360                 365
His Thr Phe Leu Asn Ile Pro Thr Gln Tyr Leu His Leu Val Ala Asp
370                 375                 380
His Tyr Phe Tyr Asn Lys His Ser Pro Val Glu Ile Arg Asp Ser Phe
385                 390                 395                 400
Leu Asp Leu Leu Gly Asp Val Leu Phe Val Pro Gly Val Val Thr
                 405                 410                 415
Ala Arg Tyr His Arg Asp Ala Gly Ala Pro Val Tyr Phe Tyr Glu Phe
             420                 425                 430
Gln His Pro Pro Gln Cys Leu Asn Asp Thr Arg Pro Ala Phe Val Lys
```

-continued

```
                    435                 440                 445
Ala Asp His Ser Asp Glu Ile Arg Phe Val Phe Gly Gly Ala Phe Leu
        450                 455                 460

Lys Gly Asp Ile Val Met Phe Glu Gly Ala Thr Glu Glu Lys Leu
465                 470                 475                 480

Leu Ser Arg Lys Met Met Arg Tyr Trp Ala Asn Phe Ala Arg Thr Gly
                485                 490                 495

Asp Pro Asn Gly Glu Gly Val Pro Leu Trp Pro Ala Tyr Thr Gln Ser
                500                 505                 510

Glu Gln Tyr Leu Lys Leu Asp Leu Ser Val Ser Val Gly Gln Lys Leu
            515                 520                 525

Lys Glu Gln Glu Val Glu Phe Trp Met Asn Thr Ile Val Pro
530                 535                 540
```

<210> SEQ ID NO 3
<211> LENGTH: 2145
<212> TYPE: DNA
<213> ORGANISM: Felis catus
<220> FEATURE:
<221> NAME/KEY: CDS
<222> LOCATION: (175)..(1803)
<220> FEATURE:
<221> NAME/KEY: misc_feature
<222> LOCATION: (1804)..(2145)
<223> OTHER INFORMATION: n is a, c, g, or t

<400> SEQUENCE: 3

```
gcggggcaat tcctctgcag atcttgggac tgatgccttt ctccaccaac cctgcatcct      60
gtgtctgcct gctcaacatt tgttgagccc tttctttctt tgactgaagc tctctgaggc     120
cagcggaggc cgtggatgtg ctaggagttc agacggtcca gccggatgag tggg atg       177
                                                              Met
                                                                1 tgg gtg cac cca ggc cgg acc ctg atc tgg gct ctt tgg gtc ctt gca       225
Trp Val His Pro Gly Arg Thr Leu Ile Trp Ala Leu Trp Val Leu Ala
        5                  10                  15 gct gtc att aag ggg cca gct gct gat gca cca gtg agg agc acc agg       273
Ala Val Ile Lys Gly Pro Ala Ala Asp Ala Pro Val Arg Ser Thr Arg
            20                  25                  30 ctg gga tgg gtc cgg ggg aag caa acc act gta ctg gga agc acc gtg       321
Leu Gly Trp Val Arg Gly Lys Gln Thr Thr Val Leu Gly Ser Thr Val
        35                  40                  45 cct gtg aac atg ttc ctc ggg atc ccc tat gct gca cct cct cta ggg       369
Pro Val Asn Met Phe Leu Gly Ile Pro Tyr Ala Ala Pro Pro Leu Gly
50                  55                  60                  65 ccc ctg cga ttt aag caa cca aag cct gct ctg ccc ggg aat gac ttc       417
Pro Leu Arg Phe Lys Gln Pro Lys Pro Ala Leu Pro Gly Asn Asp Phe
                70                  75                  80 cga aat gcc aca tcc tac cct aaa tta tgc ttc cag gac tta gag tgg       465
Arg Asn Ala Thr Ser Tyr Pro Lys Leu Cys Phe Gln Asp Leu Glu Trp
            85                  90                  95 ctg gtc tcc tat caa cac gtt ctc aaa gtg cgt tac ccc aaa ttg gaa       513
Leu Val Ser Tyr Gln His Val Leu Lys Val Arg Tyr Pro Lys Leu Glu
        100                 105                 110 gcg tcc gaa gac tgc ctg tac ctt aac atc tat gcg cca gcc cat gcg       561
Ala Ser Glu Asp Cys Leu Tyr Leu Asn Ile Tyr Ala Pro Ala His Ala
    115                 120                 125 gac aat ggc tcc aac ctc cct gtc atg gtg tgg ttc ccc ggg ggt gcc       609
Asp Asn Gly Ser Asn Leu Pro Val Met Val Trp Phe Pro Gly Gly Ala
130                 135                 140                 145
```

| | | |
|---|---|---|
| ttc aag atg ggc tca gct tcc tcc ttc gat ggg tcc gcc ttg gct gcc<br>Phe Lys Met Gly Ser Ala Ser Ser Phe Asp Gly Ser Ala Leu Ala Ala<br>150 155 160 | | 657 |
| tac gag gac gtg ctg atc gtg act acc cag tac cgg cta gga ata ttt<br>Tyr Glu Asp Val Leu Ile Val Thr Thr Gln Tyr Arg Leu Gly Ile Phe<br>165 170 175 | | 705 |
| ggt ttt ttc gac aca ggg gat gag cat gcc cgg ggg aac tgg gcc ttg<br>Gly Phe Phe Asp Thr Gly Asp Glu His Ala Arg Gly Asn Trp Ala Leu<br>180 185 190 | | 753 |
| ctg gac cag gtg gct gcc cta acc tgg gtc cgg gac aac atc gag ttc<br>Leu Asp Gln Val Ala Ala Leu Thr Trp Val Arg Asp Asn Ile Glu Phe<br>195 200 205 | | 801 |
| ttc ggt ggt gac cca cgc tcc gtg acc atc ttt gga gag tca gcg gga<br>Phe Gly Gly Asp Pro Arg Ser Val Thr Ile Phe Gly Glu Ser Ala Gly<br>210 215 220 225 | | 849 |
| gcc atc agt gtt tcc agc ctc att ctg tcc ccc ata gcc aat ggc tta<br>Ala Ile Ser Val Ser Ser Leu Ile Leu Ser Pro Ile Ala Asn Gly Leu<br>230 235 240 | | 897 |
| ttc cac aaa gcc atc atg gag agt ggg gtg gcc atc ctg cct tta ctg<br>Phe His Lys Ala Ile Met Glu Ser Gly Val Ala Ile Leu Pro Leu Leu<br>245 250 255 | | 945 |
| atg aga ccc cct ggt gat gag agg aag aag gat ttg cag gtg ctt gcg<br>Met Arg Pro Pro Gly Asp Glu Arg Lys Lys Asp Leu Gln Val Leu Ala<br>260 265 270 | | 993 |
| cgt atc tgt ggt tgc cat gcg tct gac tct gct gcc ctg ctg cag tgc<br>Arg Ile Cys Gly Cys His Ala Ser Asp Ser Ala Ala Leu Leu Gln Cys<br>275 280 285 | | 1041 |
| ctg agg gca aaa ccc tcc gag gag ttg atg gac atc agc aag aaa ctc<br>Leu Arg Ala Lys Pro Ser Glu Glu Leu Met Asp Ile Ser Lys Lys Leu<br>290 295 300 305 | | 1089 |
| acg ttt tcc att cca gtg att gat gac ttt ttc ttt cct gat gag cct<br>Thr Phe Ser Ile Pro Val Ile Asp Asp Phe Phe Phe Pro Asp Glu Pro<br>310 315 320 | | 1137 |
| gta gcc cta ttg act caa aaa gca ttt aat tca gtt cct tct atc atc<br>Val Ala Leu Leu Thr Gln Lys Ala Phe Asn Ser Val Pro Ser Ile Ile<br>325 330 335 | | 1185 |
| gga gtc aat aac cac gag tgt gcc ttc ctt ctg tcc acg gag ttt tct<br>Gly Val Asn Asn His Glu Cys Ala Phe Leu Leu Ser Thr Glu Phe Ser<br>340 345 350 | | 1233 |
| gag atc ctc ggg ggc tcc aac agg tct ctg gcc ctc tac tta gta cac<br>Glu Ile Leu Gly Gly Ser Asn Arg Ser Leu Ala Leu Tyr Leu Val His<br>355 360 365 | | 1281 |
| acg ttc ctg aat att ccc acc cag tat ttg cac ctt gtg gct gat cat<br>Thr Phe Leu Asn Ile Pro Thr Gln Tyr Leu His Leu Val Ala Asp His<br>370 375 380 385 | | 1329 |
| tac ttc tac aac aag cac tcc ccg gtt gaa ata cga gat agt ttt ctg<br>Tyr Phe Tyr Asn Lys His Ser Pro Val Glu Ile Arg Asp Ser Phe Leu<br>390 395 400 | | 1377 |
| gac ttg ctt gga gat gtg ctc ttt gtg gtc cct ggg gtg gtc aca gct<br>Asp Leu Leu Gly Asp Val Leu Phe Val Val Pro Gly Val Val Thr Ala<br>405 410 415 | | 1425 |
| cga tat cat aga gat gct ggt gca cct gtc tac ttc tat gag ttt caa<br>Arg Tyr His Arg Asp Ala Gly Ala Pro Val Tyr Phe Tyr Glu Phe Gln<br>420 425 430 | | 1473 |
| cac ccg ccc cag tgc tta aac gac acg agg cca gct ttc gtg aaa gcc<br>His Pro Pro Gln Cys Leu Asn Asp Thr Arg Pro Ala Phe Val Lys Ala<br>435 440 445 | | 1521 |
| gat cac tct gat gaa atc cgc ttc gtc ttt gga ggt gcc ttc ctg aaa<br>Asp His Ser Asp Glu Ile Arg Phe Val Phe Gly Gly Ala Phe Leu Lys<br>450 455 460 465 | | 1569 |

```
ggc gac att gtc atg ttc gaa gga gcc acc gag gag gag aaa ttg ctg    1617
Gly Asp Ile Val Met Phe Glu Gly Ala Thr Glu Glu Glu Lys Leu Leu
            470                 475                 480 agc agg aag atg atg agg tac tgg gcc aac ttt gct cgg acc ggg gac    1665
Ser Arg Lys Met Met Arg Tyr Trp Ala Asn Phe Ala Arg Thr Gly Asp
        485                 490                 495 cct aac ggg gaa ggt gtg cct ctg tgg cca gcc tac acc cag agc gag    1713
Pro Asn Gly Glu Gly Val Pro Leu Trp Pro Ala Tyr Thr Gln Ser Glu
    500                 505                 510 cag tac ctg aag ctg gat ttg agt gtg agc gtg gga cag aaa ctg aag    1761
Gln Tyr Leu Lys Leu Asp Leu Ser Val Ser Val Gly Gln Lys Leu Lys
515                 520                 525 gag caa gag gtg gag ttt tgg atg aat acc att gtc ccc tga            1803
Glu Gln Glu Val Glu Phe Trp Met Asn Thr Ile Val Pro
530                 535                 540 taccccccac ctccagggcc ctccccagtc ctccttntcc cttactctcc cttcctttgc  1863
tcccgcctgg cttnttttnt tctgctccat gggaagttct ctctgngtga tttggttttc  1923 cttttccac aatttcaccc gcggtcctta gctccgtttc tgtgtttagt ttagctactt   1983
cgtggaatca gctgctttcn ccgatgtttt atggtnttga gggtgatttt tagggaatt   2043 tcttttcaac accaaacaat gctaccggcc ttggaaggct acccgattcc ttctcctccg  2103
tgatggctgg ccaaaaaaaa aaaaaaaaaa aaaaaaaaa aa                      2145

<210> SEQ ID NO 4
<211> LENGTH: 542
<212> TYPE: PRT
<213> ORGANISM: Felis catus

<400> SEQUENCE: 4

Met Trp Val His Pro Gly Arg Thr Leu Ile Trp Ala Leu Trp Val Leu
1               5                   10                  15

Ala Ala Val Ile Lys Gly Pro Ala Ala Asp Ala Pro Val Arg Ser Thr
            20                  25                  30

Arg Leu Gly Trp Val Arg Gly Lys Gln Thr Thr Val Leu Gly Ser Thr
        35                  40                  45

Val Pro Val Asn Met Phe Leu Gly Ile Pro Tyr Ala Ala Pro Pro Leu
    50                  55                  60

Gly Pro Leu Arg Phe Lys Gln Pro Lys Pro Ala Leu Pro Gly Asn Asp
65                  70                  75                  80

Phe Arg Asn Ala Thr Ser Tyr Pro Lys Leu Cys Phe Gln Asp Leu Glu
                85                  90                  95

Trp Leu Val Ser Tyr Gln His Val Leu Lys Val Arg Tyr Pro Lys Leu
            100                 105                 110

Glu Ala Ser Glu Asp Cys Leu Tyr Leu Asn Ile Tyr Ala Pro Ala His
        115                 120                 125

Ala Asp Asn Gly Ser Asn Leu Pro Val Met Val Trp Phe Pro Gly Gly
    130                 135                 140

Ala Phe Lys Met Gly Ser Ala Ser Ser Phe Asp Gly Ser Ala Leu Ala
145                 150                 155                 160

Ala Tyr Glu Asp Val Leu Ile Val Thr Thr Gln Tyr Arg Leu Gly Ile
                165                 170                 175

Phe Gly Phe Phe Asp Thr Gly Asp Glu His Ala Arg Gly Asn Trp Ala
            180                 185                 190

Leu Leu Asp Gln Val Ala Ala Leu Thr Trp Val Arg Asp Asn Ile Glu
        195                 200                 205
```

```
Phe Phe Gly Gly Asp Pro Arg Ser Val Thr Ile Phe Gly Glu Ser Ala
    210             215                 220
Gly Ala Ile Ser Val Ser Ser Leu Ile Leu Ser Pro Ile Ala Asn Gly
225             230                 235                 240
Leu Phe His Lys Ala Ile Met Glu Ser Gly Val Ala Ile Leu Pro Leu
            245                 250                 255
Leu Met Arg Pro Pro Gly Asp Glu Arg Lys Lys Asp Leu Gln Val Leu
            260                 265                 270
Ala Arg Ile Cys Gly Cys His Ala Ser Asp Ser Ala Ala Leu Leu Gln
            275                 280                 285
Cys Leu Arg Ala Lys Pro Ser Glu Glu Leu Met Asp Ile Ser Lys Lys
        290                 295                 300
Leu Thr Phe Ser Ile Pro Val Ile Asp Asp Phe Phe Pro Asp Glu
305             310                 315                 320
Pro Val Ala Leu Leu Thr Gln Lys Ala Phe Asn Ser Val Pro Ser Ile
                325                 330                 335
Ile Gly Val Asn Asn His Glu Cys Ala Phe Leu Leu Ser Thr Glu Phe
            340                 345                 350
Ser Glu Ile Leu Gly Gly Ser Asn Arg Ser Leu Ala Leu Tyr Leu Val
        355                 360                 365
His Thr Phe Leu Asn Ile Pro Thr Gln Tyr Leu His Leu Val Ala Asp
        370                 375                 380
His Tyr Phe Tyr Asn Lys His Ser Pro Val Glu Ile Arg Asp Ser Phe
385                 390                 395                 400
Leu Asp Leu Leu Gly Asp Val Leu Phe Val Val Pro Gly Val Val Thr
                405                 410                 415
Ala Arg Tyr His Arg Asp Ala Gly Ala Pro Val Tyr Phe Tyr Glu Phe
            420                 425                 430
Gln His Pro Pro Gln Cys Leu Asn Asp Thr Arg Pro Ala Phe Val Lys
        435                 440                 445
Ala Asp His Ser Asp Glu Ile Arg Phe Val Phe Gly Gly Ala Phe Leu
450                 455                 460
Lys Gly Asp Ile Val Met Phe Glu Gly Ala Thr Glu Glu Lys Leu
465                 470                 475                 480
Leu Ser Arg Lys Met Met Arg Tyr Trp Ala Asn Phe Ala Arg Thr Gly
            485                 490                 495
Asp Pro Asn Gly Glu Gly Val Pro Leu Trp Pro Ala Tyr Thr Gln Ser
            500                 505                 510
Glu Gln Tyr Leu Lys Leu Asp Leu Ser Val Ser Val Gly Gln Lys Leu
        515                 520                 525
Lys Glu Gln Glu Val Glu Phe Trp Met Asn Thr Ile Val Pro
        530                 535                 540
```

CAT KIDNEY DISEASE MARKER

This application is a divisional of U.S. application Ser. No. 10/233,933, filed Sep. 3, 2002 now U.S. Pat. No. 7,026,151.

TECHNICAL FIELD

The present invention relates to a newly identified polypeptide (or protein) and a polynucleotide (or nucleic acid) (or a part thereof), inclusive of salts thereof, which are useful as markers for diagnosing feline nephropathy; mutants and derivatives of the polypeptide (or protein) and of the polynucleotide (or nucleic acid); methods of producing the polypeptide (or protein) and polynucleotide (or nucleic acid), or mutants or derivatives thereof, an antibody to the polypeptide (or protein) (or a part thereof), an immunological assay method using the antibody, and a reagent to be used therefor; and the use (inclusive of the use as a diagnostic reagent, or in a diagnostic method, for instance) of those in diagnosis of feline nephropathy. The present invention also relates to a diagnostic method which comprises making a diagnosis of nephropathy frequently encountered in family cats by assaying a urinary protein (cauxin).

BACKGROUND ART

Under considerable daily stresses of life in these days, those individuals who wish to live with a pet are increasing in number, and the number of pet dogs and cats is increasing year after year. On the other hand, with the advancement in veterinary medicine and popularization of pet foods, the number of dogs and cats of advanced age is increasing and, like in humans, the incidence of adult diseases, obesity and nephropathy (renal diseases), among others, is increasing, raising a serious problem. As regards nephropathy, in particular, it is very difficult to recognize a disease signal at an early stage, as suggested by the saying that the kidney is a silent organ. Therefore, upon veterinary examination in view of some or other symptoms, the renal function is found to be in severe disorder in many instances.

In clinical veterinary medicine, the cases of renal diseases have been increasing in recent years with the aging of animals of the family Felidae and, at present, nephropathy is the primary cause of death among family cats. Further, the symptoms of nephropathy are noticed in most cases only when they are already in advanced stages and, thus, the disease is often already in an incurable stage at the time of consultation with a veterinarian. Thus, chronic renal failure is ranked high in the list of causes of deaths of cats.

The clinical symptoms of nephropathy, in particular chronic renal failure, are such general or constitutional symptoms as polyposia and polyuria, anorexia, weight loss, vomiting, diarrhea, dehydration, anemia, and depression. Diagnosis is carried out by or according to an interview with the owner, urinalysis, blood examination, renal biopsy, and imaging, among others. As general indicators of nephropathy, there may be mentioned blood urea nitrogen (hereinafter, BUN), serum creatinin (hereinafter, CRE), and proteinuria. However, accelerative increases in both BUN and CRE are observed only after a decrease in glomerular filtration value (an index in renal function evaluation) to 25% of the normal level or below, hence they cannot serve as markers for early diagnosis. In addition, the BUN is influenced by meals, and the CRE by physical activity. As for the urinary protein, or proteinuria, it is one of findings suggesting disorders of kidneys and is so important that when it is found, nephropathy is suspected first of all. However, while the protein excretion in normal human urine is 3 mg or less/kg/day, the protein excretion in feline urine is as high in concentration as 17.43±9.03 mg/kg/day even in normal conditions. Thus, the equation proteinuria=nephropathy can hardly be formulated.

Under such circumstances, the advent of a marker for early diagnosis of feline nephropathy is now earnestly desired.

The conventional methods of diagnosing nephropathy mainly utilize such complicated techniques as blood examination, radiography of kidneys using a contrast medium, ultrasonic image analysis, and so forth. It is demanded that a more easy and simple method be developed. Further, it is desired that a method by which the owner can check the health status of a cat in a simple and easy manner without visiting a veterinarian and a test kit therefor be developed. A convenient test reagent is also required with which feline nephropathy can easily be found before the disease becomes incurable, with the result that the life of a family cat can be prolonged.

DISCLOSURE OF INVENTION

The present inventors have so far made investigations on the theme of feline nephropathy resulting from advanced age and, thus, concerning a method of diagnosing feline nephropathy by urinary protein analysis utilizing SDS-PAGE. In the course thereof, they discovered a novel protein (named cauxin by them) having a molecular weight of 70 K and excreted in feline urine in high concentrations in normal adult cats showing no clinical abnormality, and examined the concentrations of cauxin excreted in urine in cats with various diseases. As a result, it was confirmed that cats already in the state of renal failure show markedly decreased urinary concentrations of cauxin. Thus, they proceeded with the analysis of cauxin as a novel marker for diagnosing nephropathy. Further, they determined the nucleotide base sequence of the cauxin gene and the amino acid sequence of cauxin and thus revealed that the nucleotide base sequence determined has 47% homology with the carboxylesterase family, that cauxin has carboxylesterase activity, and that, unlike other carboxylesterases, it is expressed in vivo specifically in the epithelial cells of distal kidney tubules. Thus, they were led to a recognition that cauxin is not a serum protein-derived urinary protein but a novel carboxylesterase-like protein produced in distal kidney tubule epithelial cells and secreted into tubular cavities from the apical side and excreted into urine. Further investigations based on the utility as a marker for diagnosing feline nephropathy have now led to completion of the present invention.

The novel diagnostic marker according to the present invention, which is produced specifically in renal tubular tissues and excreted into urine, creates the possibility of renal tissue disorders being found at an early stage and the possibility of remaining normal tubular tissues in diseased kidneys being quantitatively grasped. Therefore, it is considered to be a very useful item from the clinical viewpoint.

The present invention provides:

[1] A protein characterized by its being cauxin, or a salt thereof;

[2] A protein or a salt thereof as defined above under [1] which is characterized by its serving as a marker for diagnosing feline nephropathy;

[3] A protein or a salt thereof as defined above under [1] or [2] which is characterized by (a) having at least the sequence $Asp^{26}$ to $Pro^{542}$ out of the amino acid sequence shown under SEQ ID NO: 2 in the sequence listing, or
(b) having the amino acid sequence shown under SEQ ID NO: 2 in the sequence listing, or
(c) having at least 50% homology with the sequence $Asp^{26}$ to $Pro^{542}$ out of the amino acid sequence shown under SEQ ID NO: 2 in the sequence listing or having at least 50% homology with the amino acid sequence shown under SEQ ID NO: 2 in the sequence listing;

[4] A partial peptide of the protein defined above under any of [1] to [3];

[5] A nucleic acid characterized by having a nucleotide base sequence coding for the protein defined above under any of [1] to [3] or the partial peptide defined above under [4];

[6] A nucleic acid as defined above under [5] which is characterized by
(a) having the nucleotide base sequence shown under SEQ ID NO: 1 in the sequence listing,
(b) having the nucleotide base sequence shown under SEQ ID NO: 3 in the sequence listing,
(c) having at least the sequence from the 250th nucleotide base to the 1803rd nucleotide base out of the nucleotide base sequence shown under SEQ ID NO: 3 in the sequence listing,
(d) being capable of hybridizing with a sequence having any of the nucleotide base sequences defined above under (a) to (c) under stringent conditions, or
(e) being capable of hybridizing with a nucleotide base sequence comprising ten or more consecutive nucleotide bases out of the nucleotide base sequence shown under SEQ ID NO: 1 or SEQ ID NO: 3 in the sequence listing;

[7] A vector characterized by containing the nucleic acid defined above under [5] or [6];

[8] A transformant characterized by harboring the nucleic acid defined above under [5] or [6] or the vector defined above under [7];

[9] A method of obtaining the protein defined above under any of [1] to [3] or the partial peptide defined above under [4] which comprises cultivating the transformant defined above under [8] and recovering the product from the culture;

[10] An antibody characterized by being capable of specifically binding to the protein defined above under any of [1] to [3] or the partial peptide defined above under [4];

[11] A method of diagnosing feline nephropathy which comprises quantitatively assaying for urinary cauxin and detecting feline nephropathy with using as an index a decrease in the level of cauxin;

[12] A method of diagnosing feline nephropathy as defined above under [11] which comprises
(i) the step of subjecting a urinary protein-containing sample to separation by electrophoresis, or
(ii) the step of assaying for a biological urinary cauxin activity, or
(iii) the step of bringing a urinary protein-containing sample into contact with an anti-cauxin antibody;

[13] A diagnostic agent for feline nephropathy which comprises
(i) a cauxin-staining agent, or
(ii) a reagent for assaying for a biological urinary cauxin activity, or
(iii) an anti-cauxin antibody;

[14] A cauxin detecting kit which comprises
(a) a sample application site, (b) a labeled antibody-containing site, (c) an antigen detection site and (d) a reaction completion judging site, as disposed in that order on a carrier or support enabling substances to move in a wet condition, wherein
(i) the labeled antibody-containing site contains a labeled anti-cauxin antibody (labeled antibody) which is capable of migrating on the carrier to the antigen detection site and then to the reaction completion judging site in a wet condition,
(ii) an immobilized anti-cauxin antibody (immobilized antibody) is placed on the detection site, and
(iii) a site where an antibody (second antibody) to the antibody used as the labeled antibody is immobilized is formed on the reaction completion judging site, and wherein
when a sample is applied to the sample application site, the sample is allowed to migrate on the carrier, elute the labeled antibody and pass through the immobilized antibody on the antigen detection site and through the second antibody site on the reaction completion judging site, for detecting cauxin in the sample;

[15] A cauxin detecting kit for the assay of cauxin in a sample which is characterized in that a sample is brought into contact with a substrate for carboxylesterase and the resulting signal is measured; and

[16] A cauxin detecting kit characterized in
(1) that a sample is brought into contact with an immobilized anti-cauxin antibody and then with a labeled anti-cauxin antibody or
(2) that a sample is brought into contact with a labeled anti-cauxin antibody and then an immobilized anti-cauxin antibody, and cauxin is assayed utilizing the label as an indicator.

Other objects, features, advantages and viewpoints of the present invention will become apparent to those skilled in the art in view of the description which follows. It is to be understood, however, that the description in the present specification, including the subsequent description and the description of specific examples, is given for illustrating preferred embodiments of the present invention and only for illustrative purposes alone. It will be quite obvious to those skilled in the art that various changes and/or improvements (or modifications) can be made within the spirit and scope of the present invention as disclosed herein based on the subsequent description and the knowledge obtainable from other portions of the present specification. All the patent documents and references cited herein have been cited for the purpose of illustration and the contents therein shall be construed as constituting a part of and being contained in the present specification.

BRIEF DESCRIPTION OF THE DRAWINGS

FIG. 4 shows the C-terminal amino acid sequence alignment of cauxin as shown in comparison with carboxylesterases obtained from rat kidney, rat liver, swine liver and human liver.

FIG. 9C is a tissue photograph illustrating the in situ hybridization (×100) patterns of a corticomedullar transitional zone of an adult cat kidney, FIG. 9D is an enlargement (in situ hybridization (×400)) of the site shown in FIG. 9C, and FIG. 9E is a tissue photograph illustrating the in situ hybridization (×200) patterns of a corticomedullar transitional zone of an adult cat kidney.

BEST MODES FOR CARRYING OUT THE INVENTION

Figure 1:
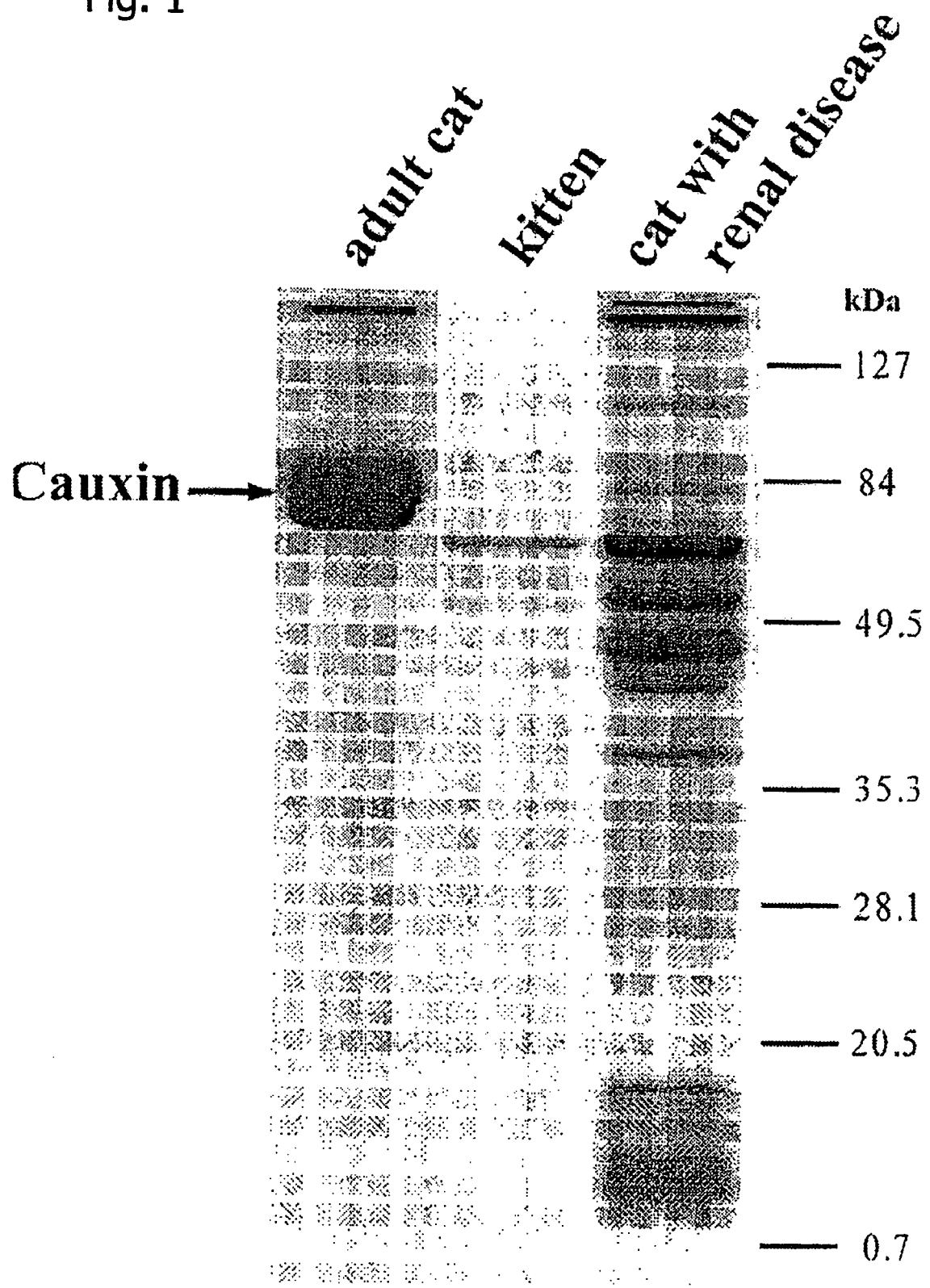
FIG. 1 is a photograph showing the SDS-polyacrylamide electrophoresis profiles of feline urinary proteins.

Cauxin occurs in high concentrations in urine under normal conditions while the urinary level of cauxin decreases with the decrease in renal functions. By taking into consideration the extent of decrease in its level, it becomes possible to estimate the amount of tissues performing normal renal functions. Thus, it is desirable that the assay be quantitative, not qualitative. The sample to be used for cauxin assay is urine, and the cauxin concentration in urine is influenced by the amount of urine. Therefore, for avoiding the influence on the amount of urine, the ratio of cauxin to urinary creatinine or urinary protein, for instance, is preferably determined.

In the practice of the present invention, the cauxin assaying kit, for instance, is preferably so constituted that it can be used in the manner of (A) screening, (B) diagnosis, or (C) routine control. The assaying mode may be either a simplified one or an exact one. In the simplified mode, the cat keepers, for instance, can be regarded as users, and the kit may be of the stick type enabling rough estimation of the cauxin level according to the extent of coloration, of the sheet type to be laid on the toilet for a cat, or of the small bead type to be used in admixture with the sand for use in the toilet for a cat. In the exact mode, it is allowed that the user is restricted to a veterinarian, for instance, and the kit may be of the liquid type for use in assaying on an automated analyzer.

The assay method may be either the one measuring the enzyme activity or the one using the antigen-antibody interaction. In particular, techniques involving an immunological method are preferred.

The present invention provides cauxin polypeptide or a salt thereof, a peptide, inclusive of salts thereof, having at least 50% homology with the amino acid sequence of the cauxin polypeptide and having carboxylesterase activity or comparable antigenicity, a partial peptide, inclusive of salts thereof, characteristic of the polypeptide, genes coding therefor, for example DNAs and RNAs, vectors or plasmids containing such a gene in a manner such that the gene can be manipulated by the gene recombination technology, host cells transformed with such a vector or the like, further transgenic animals, such as transgenic mice, in which such a gene is expressed, knockout animals, such as knockout mice, in which such gene has been specifically inactivated, a method of producing the relevant polypeptide or a salt thereof by cultivating such transformant cells, antibodies, in particular monoclonal antibodies, obtained by using the thus-obtained polypeptide or a salt thereof, or a characteristic partial peptide of that polypeptide or a salt thereof, hybridoma cells producing such an antibody, as well as assaying/diagnosing means and reagents which use such a gene isolated, for example a DNA or RNA, as a probe or use such an antibody. Furthermore, there are provided the uses of those active ingredients disclosed and described herein, for example pharmaceutical preparations or reagents containing such active ingredients, and methods for the treatment and/or prophylaxis of diseases, disorders or abnormal conditions using such active ingredients and, further, relevant screening methods and so forth.

The term "cauxin" as used herein refers to a novel peptide found for the first time as a 70 K protein in the urine of adult cats and disclosed in the present specification. Cauxin is a peptide composed of 542 amino acid residues and is characterized in that it lacks the region of endoplasmic reticulum retention signal (HXEL), which carboxylesterases have, on the C-terminal side. In view of its similarity to carboxylesterases, it is estimated to have carboxylesterase activity and further estimated to have some or other activity in the metabolism of lipids in cats. Thus, cauxin includes, within the meaning thereof, species having carboxylesterase activity.

The term "polypeptide" as used herein may refer to any of the polypeptides described later herein. The fundamental structures of polypeptides are well known in the art and are described in a very large number of reference books and other publications in the relevant field of art. In view of such situation, the term "polypeptide" as used herein refers to any peptide or any protein comprising two or more amino acid residues bonded together via peptide bonding or modified peptide bonding. The term "polypeptide" as used herein includes both the short-chain ones also referred to as peptides, oligopeptides or peptide oligomers and the long-chain ones generally referred to as proteins and known to occur in various shapes and forms.

The polypeptide may often contain an amino acid(s) other than the 20 amino acids generally called natural amino acids (naturally occurring amino acids; or amino acids encoded by genetic codes). It will be understood that a large number of amino acid residues, including the terminal amino group, of the polypeptide can be altered (modified) not only by a natural step such as posttranslational processing and/or other alteration (or modification) but also by some or other chemical modification technology well known in the art. Various alterations (modifications) applicable to the polypeptide are known and described in detail in basic reference books, detailed study reports and a large number of scientific documents and thus well known to those skilled in the art. As several, in particular conventional, alterations/modifications, there may be mentioned glycosylation, lipid binding, sulfation, γ-carboxylation with a glutamic acid residue, hydroxylation, and ADP-ribosylation, among others, and the descriptions in T. E. Creighton, Proteins—Structure and Molecular Properties, Second Edition, W. H. Freeman and Company, New York, (1993); B. C. Johnson (Ed.), Posttranslational Covalent Modification of Proteins, Academic Press, New York, (1983) (Wold, F., "Posttranslational Protein Modifications: Perspective and Prospects", pp. 1-12); Seifter et al., "Analysis for Protein Modifications and nonprotein cofactors", Meth. Enzymol. 182: 626-646 (1990); Rattan et al., "Protein Synthesis: Posttranslational Modification and Aging", Ann. N.Y. Acad. Sci., 663: pp. 48-62 (1992), for instance, can be referred to.

The "polypeptide" of the present invention includes, among others, cauxin and related polypeptides. The cauxin and related polypeptides include all of those derived from animals of the family Felidae, those having carboxylesterase activity or activity involved in lipid metabolism, typically those observed in normal adult cats (family cats), showing decreases in urinary excretion in kittens or cats suffering from nephropathy and forming a band at about 70 K in SDS-PAGE and, more specifically, those having an amino acid sequence which has at least 50% homology with the amino acid sequence shown under SEQ ID NO: 2 in the sequence listing and being substantially equivalent thereto in biological activities such as carboxylesterase activity and/or antigenicity.

The "cauxin" of the present invention may be one having carboxylesterase activity, or one having a novel amino acid sequence highly homologous with the amino acid sequence shown under SEQ ID NO: 2 in the sequence listing. As more preferred peptides of the present invention, there may be mentioned those having 10 or more, preferably 20 or more, consecutive amino acid residues selected from the amino acid sequence shown under SEQ ID NO: 2 in the sequence listing. The peptide of the present invention may have part or all of the amino acid sequence shown under SEQ ID NO: 2 in the sequence listing, and includes all of those having such a sequence. As preferred examples, there may be mentioned those having at least the sequence from $Asp^{26}$ to $Pro^{542}$, or a part thereof, out of the sequence shown under SEQ ID NO: 2 in the sequence listing.

In the present specification, "homology" refers to the quantity (number) of those corresponding amino acid residues or nucleotide bases between two polypeptide sequence (or amino acid sequence) or polynucleotide sequence (or base sequence) chains which can be judged as the same in their matching relationship, and thus means the degree of sequence similarity or relatedness between two polypeptide sequences or two polynucleotide sequences. The homology can easily be calculated. A number of methods of determining the homology between two polynucleotide sequences or polypeptide sequences are known, and the term "homology" (also referred to as "similarity") is well known in the art (e.g. Lesk, A. M. (Ed.), Computational Molecular Biology, Oxford University Press, New York, (1988); Smith, D. W. (Ed.), Biocomputing; Informatics and Genome Projects, Academic Press, New York, (1993); Grifin, A. M. & Grifin, H. G. (Ed.), Computer Analysis of Sequence Data: Part I, Human Press, New Jersey, (1994); von Heinje, G., Sequence Analysis in Molecular Biology, Academic Press, New York, (1987); Gribskov, M. & Devereux, J. (Ed.), Sequence Analysis Primer, M-Stockton Press, New York, (1991), etc.).

The general methods to be used in determining the homology between two sequences include, but are not limited to, those disclosed in Martin, J. Bishop (Ed.), Guide to Huge Computers, Academic Press, San Diego, (1994); Carillo, H. & Lipman, D., SIAM J. Applied Math., 48: 1073 (1988), and so forth. Preferred as the method of homology estimation is the one which has been designed to find out the maximum matching relation between two sequences to be tested. As such method, there may be mentioned those formulated as computer programs. Preferred computer programs for estimating the homology between two sequences include, but are not limited to, the GCG program package (Devereux, J. et al., Nucleic Acids Research, 12 (1): 387 (1984)), BLASTP, BLASTN, FASTA (Atschul, S. F. et al., J. Molec. Biol., 215: 403 (1990)), etc. Any of those known in the relevant field of art can be used.

In accordance with the present invention, the gene coding for cauxin is typically one having a nucleotide base sequence coding for the peptide shown under SEQ ID NO: 2 in the sequence listing or a partial consecutive amino acid sequence thereof, for example one having the nucleotide base sequence shown under SEQ ID NO: 1 in the sequence listing, or may be one resulting from addition of an initiation codon, for example the codon coding for Met (and a termination codon), to such nucleotide base sequence, one having a nucleotide base sequence coding for a peptide having an amino acid sequence showing at least 80% homology with the protein encoded by the nucleotide base sequence mentioned above and having carboxylesterase activity or a peptide substantially equivalent in biological activities, for example antigenicity, thereto, or one having a nucleotide base sequence equivalent to such nucleotide base sequence. The cauxin-encoding gene may be in the form of single-stranded DNA, double-stranded DNA, RNA, DNA:RNA hybrid, synthetic DNA or a like nucleic acid, and may be a cDNA derived from feline genomic DNA, a feline genomic DNA library, or tissues or cells of an animal of the family Felidae, or a synthetic DNA. The nucleotide base sequence of the cauxin-encoding gene may be modified (e.g. by addition, deletion or substitution), and the gene in question may include such modifications. As described later herein, the nucleic acid of the present invention may also be one coding for the peptide of the present invention or a part thereof, and preferably is a DNA. As the above-mentioned "equivalent nucleotide base sequence", there may be mentioned those capable of hybridizing with a nucleotide base sequence comprising 10 or more, preferably 20 or more consecutive nucleotide bases selected from the nucleotide base sequence shown under SEQ ID NO: 1 or SEQ ID NO: 3 in the sequence listing under stringent conditions and coding for an amino acid sequence substantially equivalent to cauxin.

In accordance with the present invention, gene recombination technologies can be used to isolate and sequence the desired nucleic acid, construct recombinants thereof, and produce the desired peptide. The gene recombination technologies (inclusive of recombinant DNA technologies) can be carried out by the methods described, for example, in J. Sambrook, E. F. Fritsch & T. Maniatis, "Molecular Cloning: A Laboratory Manual (2nd edition)", Cold Spring Harbor Laboratory Press, Cold Spring Harbor, N.Y. (1989); D. M. Glover et al. ed., "DNA Cloning", 2nd ed., Vols. 1 to 4, (The Practical Approach Series), IRL Press, Oxford University Press (1995); Japanese Biochemical Society (ed.), "Zoku Seikagaku Jikken Koza (Experiments in Biochemistry, Second Series) 1, Idenshi Kenkyuho (Methods of Gene Studies) II", Tokyo Kagaku Dozin (1986); Japanese Biochemical Society (ed.), "Shin Seikagaku Jikken Koza (Experiments in Biochemistry, Updated) 2, Kakusan (Nucleic Acids) III (Recombinant DNA Technology)", Tokyo Kagaku Dozin (1992); R. Wu ed., "Methods in Enzymology", Vol, 68 (Recombinant DNA), Academic Press, New York (1980); R. Wu et al. ed., "Methods in Enzymology", Vol. 100 (Recombinant DNA, Part B) & Vol. 101 (Recombinant DNA, Part C), Academic Press, New York (1983); R. Wu et al. ed., "Methods in Enzymology", Vol. 153 (Recombinant DNA, Part D), Vol. 154 (Recombinant DNA, Part E) & Vol. 155 (Recombinant DNA, Part F), Academic Press, New York (1987); J. H. Miller ed., "Methods in Enzymology", Vol. 204, Academic Press, New York (1991); R. Wu et al. ed., "Methods in Enzymology", Vol. 218, Academic Press, New York (1993); S. Weissman (ed.), "Methods in Enzymology", Vol. 303, Academic Press, New York (1999); and J. C. Glorioso et al. (ed.), "Methods in Enzymology", Vol. 306, Academic Press, New York (1999), or methods substantially identical thereto, or modifications thereof (the relevant descriptions in these references are incorporated herein by reference) [hereinafter all of these are collectively referred to as "gene recombination technology"].

The term "polymerase chain reaction" or "PCR" as used herein generally refers to such a method as described in U.S. Pat. No. 4,683,195 and, for example, refers to a method for enzymatically amplifying a desired oligonucleotide sequence in vitro. Generally, PCR comprises repetitions of a cycle for nucleotide sequence synthesis by primer extension using two oligonucleotide primers capable of preferentially hybridizing with a template nucleic acid. Typically, the primers to be used in PCR may be primers complementary to the nucleotide sequence to be amplified in the template and, for example, those complementary at both ends of the nucleotide sequence to be amplified or adjacent to the nucleotide sequence to be amplified are preferably used. The 5' end side primer is preferably selected so that it contains at least the initiation codon or amplification inclusive of the initiation codon can be carried out, while the 3' end side primer is preferably selected so that it contains at least the stop codon or amplification inclusive of the stop codon can be carried out. Preferred as the primers are oligonucleotides comprising 18 to 25 nucleotide bases. The primers can be prepared by the methods well known in the art. Typically, they can be chemically synthesized by those known methods described in Angew. Chem. Int. Ed. Engl., Vol. 28, pp. 716-734 (1989), for example the phosphotriester method, phosphodiester method, phosphite method, phosphoamidite method, and phosphonate method. It is generally known that such synthesis can be conveniently carried out on a modified solid supporting member using, for example, an automated synthesizer, such as a model 381A DNA synthesizer (Applied Biosystems). The oligonucleotides may contain one or more modified nucleotide bases, for example inosine or a like nucleotide base nonconventional in the nature, or a tritylated nucleotide base.

The PCR can be carried out by the methods known in the art, methods substantially identical thereto, or modifications thereof, for example the method described in R. Saiki, et al., Science, 230: 1350, 1985; R. Saiki, et al., Science, 239: 487, 1988; H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995); M. A. Innis et al. ed., "PCR Protocols: a guide to methods and applications", Academic Press, New York (1990); M. J. McPherson, P. Quirke and G. R. Taylor (Ed.), PCR: a practical approach, IRL Press, Oxford (1991); M. A. Frohman et al., Proc. Natl. Acad. Sci. USA, 85, 8998-9002 (1988), etc., or modifications or improved versions thereof The PCR method can also be carried out using commercially available kits suited therefor according to the protocols disclosed by kit manufacturers or kit distributors.

The PCR product obtained is generally subjected to 1 to 2% agarose gel electrophoresis, specific bands are excised from the gel, and DNA is extracted using a commercial extraction kit such as a gene clean kit (Bio 101), for instance. The DNA extracted is cleaved with an appropriate restriction enzyme(s) and, after purification treatment, and, if necessary, after further phosphorylation at the 5' end using T4 polynucleotide kinase or the like, the fragment obtained is ligated to an appropriate vector such as pUC18 or a like pUC vector for use in transformation of appropriate competent cells. The PCR product clones is analyzed for its nucleotide base sequence. For cloning the PCR product, such commercial plasmid vectors as p-Direct (Clontech), pCR-Script™ SK(+) (Stratagene), PGEM-T (Promega) and pAmp™ (Gibco-BRL), for instance, can be used. For transforming host cells, those methods known in the relevant field of art or methods substantially equivalent thereto can be used, for example using a phage vector or by the calcium method, rubidium/calcium method, calcium/manganese method, TFB high efficiency method, FSB frozen competent cell method, rapid colony method, or electroporation (D. Hanahan, J. Mol. Biol., 166: 557, 1983, etc.). For isolating the desired DNA, polymerase chain reaction coupled reverse transcription (RT-PCT) or RACE (rapid amplification of cDNA ends) can be applied. The RACE can be carried out according to the method described in M. A. Innis et al. ed., "PCR Protocols" (M. A. Frohman, "a guide to methods and applications"), pp. 28-38, Academic Press, New York (1990), for instance.

For nucleic acid identification, for instance, such a hybridization technique as mentioned below is utilized.

The DNA obtained can be cloned, if necessary, and, for example, a plasmid, λ phage, cosmid, P1 phage, F factor, YAC or the like can be used for that purpose. Preferred are λ phage-derived vectors and, thus, Charon 4A, Charon 21A, λ gt10, λgt11, λDASHII, λFUXII, λEMBL3, λZAPII™ (Stratagene) and the like can be utilized. Further, the DNA obtained may be inserted into an appropriate vector, for example the plasmid pEX, pMAMneo or pKG5, for expression thereof in appropriate host cells, such as *Escherichia coli,* yeast cells, CHO cells, or COS cells, as explained later herein in detail. Further, the DNA fragment, either as it is or as a DNA fragment resulting from addition of an appropriate regulatory sequence, can be inserted into an appropriate vector and then introduced into an animal to produce a transgenic animal in which the desired gene, for example the propeptide-deficient pro-MMP-7 or C terminal-deficient CD151, is expressed. As such animal, there may be mentioned mammals such as mice, rats, rabbits, guinea pigs and bovine species. Preferably, the gene fragment can be introduced into fertilized animal (e.g. mouse) eggs to produce transgenic animals. The foreign gene can be introduced into mammalian or like animal cells by the methods known in the art or method substantially equivalent thereto, for example by the calcium phosphate method (e.g. F. L. Graham et al., Virology, 52: 456, 1973), DEAE-dextran method (e.g. D. Warden et al., J. Gen. Virol., 3: 371, 1968), electroporation (e.g. E. Neumann et al., EMBO J., 1:841, 1982), microinjection, ribosome method, viral infection, phage particle method, etc. The gene product produced by animal cells thus transfected with the intended gene can also be analyzed.

The plasmid into which the intended gene (e.g. DNA obtained in according to the present invention) is to be inserted may be any of those plasmids which allow the DNA to be expressed in host cells commonly used in genetic engineering (e.g. prokaryotic host cells such as *Escherichia coli* or *Bacillus subtilis*, eukaryotic host cells such as yeasts, CHO cells or COS cells, or insect cells such as Sf21). Such a sequence may contain, for example, a codon(s) adequately modified for the expression in the host cells selected, a restriction enzyme site, a regulatory sequence and a promoter sequence for facilitating the expression of the gene in question, a linker(s) or adapter(s) serving in ligation of the gene in question, and, further, a sequence (including a sequence coding for a hybrid protein or a fused protein) useful in regulating or controlling an antibiotic resistance or metabolism or in selection. An appropriate promoter may preferably be used, for example the tryptophan promoter (trp), lactose promoter (lac), tryptophan lactose promoter (tac), lipoprotein promoter (lpp), λ phage $P_L$ promoter or the like in plasmids for which *Escherichia coli* cells serve as hosts, the SV40 late promoter, MMTV LTR promoter, RSV LTR promoter, CMV promoter, SRα promoter or the like in plasmids for which animal cells serve as hosts, or the GAL1 or GAL10 promoter or the like in plasmids for which yeast cells serve as hosts.

As plasmids for which *Escherichia coli* serves as a host, there may be mentioned, for example, pBR322, pUC18, pUC19, pUC118, pUC119, pSP64, pSP65, pTZ-18R/-18U, pTZ-19R/-19U, pGEM-3, pGEM-4, pGEM-3Z, pGEM-4Z, pGEM-5Zf(−), pBluescript KS™ (Stratagene), etc. As plasmid vectors suited for expression in *Escherichia coli*, there may also be mentioned pAS, pKK223 (Pharmacia), pMC1403, pMC931, pKC30, PRSET-B (Invitrogen), etc. As plasmids for which animal cells serve as hosts, there may be mentioned the SV40 vector, polyoma virus vectors, vaccinia virus vectors, retrovirus vectors and the like, for example pcD, pcD-SRα, CDM8, pCEV4, pME18S, pBC12BI, pSG5 (Stratagene), etc. As plasmids for which yeasts serve as hosts, there may be mentioned YIp type vectors, YEp type vectors, YRp type vectors, YCp type vectors and the like, for example pGPD-2. As for the host cells, when the host is *Escherichia coli*, there may be mentioned *Escherichia coli* K12 strain-derived strains such as NM533, XL1-Vlue, C600, DH1, DH5, DH11S, DH12S, DH5α, DH10B, HB101, MC1061, JM109 and STBL2, and BL21(DE3)pLysS and the like as B834 stain-derived ones. When the host cells are animal cells, there may be mentioned, for example, African green monkey fibroblast-derived COS-7 cells, COS-1 cells, CV-1 cells, mouse fibroblast-derived COP cells, MOP cells, WOP cells, Chinese hamster cell-derived CHO cells, CHO DHFR cells, human HeLa cells, murine cell-derived C127 cells, murine cell-derived NIH 3T3 cells, etc. As for the insect cells, mention may be made of the use of silkworm larvae or cultured silkworm cells, for example BM-N cells, together with *Bombyx mori* nuclear polyhedrosis virus or a derivative thereof as the vector. It is also possible to use plant cells as host cells, which, together with adequate vectors, are widely known in the relevant field of art. In the genetic engineering technique according to the present invention, use can be made of those restriction enzymes, reverse transcriptases, DNA modifying or decomposing enzymes for modifying or converting DNA fragments to structures suited for cloning, DNA polymerases, terminal nucleotidyl transferases, DNAs and ligases which are known or in wide use in the relevant field.

In accordance with the present invention, a cell line having high and stable expression capacity can be obtained by subjecting a transformant obtained by transformation with an expression vector containing a protein-encoding nucleic acid to repeated cloning using an appropriate selective marker as necessary. For example, when the dhfr gene is utilized as the selective marker in transformant cells derived from animal cells used as host cells, a cell line capable of amplifying a DNA coding for the protein according to the invention and thus causing a higher level of expression can be obtained by carrying out cultivation while the MTX concentration is gradually increased and selecting a resistant strain. When cultured under conditions enabling the expression of a nucleic acid coding for the protein of the present invention, the transformant of the present invention can produce and accumulate the desired product therein. For cultivating a transformant derived from a prokaryotic cell host such as *Escherichia coli* or *Bacillus subtilis* or from a yeast, for instance, a liquid medium can suitably be used. The medium is caused to contain a carbon source(s), a nitrogen source(s), inorganic substances and so forth which are necessary for the growth of the transformant. The carbon source includes, among others, glucose, dextrin, soluble starch, and sucrose, the nitrogen source includes, among others, ammonium salts, nitrate salts, corn steep liquor, peptone, casein, meat extract, malt extract, soybean cake, potato extract and like inorganic or organic substances, the inorganic substances include, among others, calcium chloride, sodium dihydrogen phosphate, magnesium chloride, and calcium carbonate. Yeasts, vitamins, casamino acids, growth promoters and the like may also be added. If necessary, for more efficient promoter functioning, such an agent as 3 β-indolylacrylic acid, for instance, may be added. The medium preferably has a pH of about 5 to 8.

In the case of *Escherichia coli*, for instance, the cultivation is generally carried out at about 15 to about 45° C. for about 3 to about 75 hours. If necessary, aeration and/or stirring may be carried out additionally. For cultivating a transformant derived from animal cells as host cells, the medium to be used is, for example, about 5 to about 20% fetal bovine serum-containing MEM medium, PRMI 1640 medium, or DMEM medium. The pH is preferably about 6 to about 8. The cultivation is generally carried out at about 30° C. to about 40° C. for about 15 to about 72 hours, if necessary with aeration and/or stirring. The transformant expressing the desired gene product may be utilized as it is or in the form of a cell homogenate, or the desired gene product can be isolated for use thereof In extraction from the cells cultured in the above manner, any adequate method be used. For example, after cultivation, the microbial or other cells are collected by a conventional method, suspended in an appropriate buffer solution, and disrupted by sonication, with lysozyme and/or by freezing and thawing, for instance, and a crude extract is recovered by centrifugation or filtration. To the buffer solution, there may be added a protein denaturing agent such as urea or guanidine hydrochloride, and/or a surfactant such as Triton X-100 (trademark) or Tween 20 (trademark). In cases where the desired product is secreted into the culture fluid, the culture fluid after completion of cultivation is separated into the microbial or other cells and the supernatant by a per se known method, and the supernatant is collected. The desired product contained in the thus-obtained culture supernatant or extract can be purified by an appropriate combination of per se known methods of separation and purification, for example salting out with ammonium sulfate, for instance, gel filtration using Sephadex, ion exchange chromatography using a carrier having diethylaminoethyl or carboxymethyl groups, for instance, hydrophobic chromatography using a carrier having such hydrophobic groups as butyl, octyl, or phenyl groups, dye gel chromatography, electrophoresis, dialysis, ultrafiltration, affinity chromatography, and high-performance liquid chromatography. Preferably, the product can be purified and isolated by such treatment as polyacrylamide gel electrophoresis, or affinity chromatography utilizing an immobilized ligand or the like. Thus, gelatin-agarose affinity chromatography and heparin-agarose chromatography may be mentioned among others.

Further, mutant proteins corresponding to the protein in question as resulting from substitution, deletion, insertion, translocation and/or addition of one or a plurality of amino acid residues can be produced based on the nucleotide base sequence of the gene according to the present invention by using a method(s) generally used in genetic engineering. As the methods of such mutation, conversion or modification, there may be mentioned the methods described, or example, in Japanese Biochemical Society (ed.), "Zoku Seikagaku Jikken Koza (Experiments in Biochemistry, Second Series) 1, Idenshi Kenkyuho (Methods of Gene Studies) II", p. 105 (Susumu Hirose), Tokyo Kagaku Dozin (1986); Japanese Biochemical Society (ed.), "Shin Seikagaku Jikken Koza (Experiments in Biochemistry, Updated) 2, Kakusan (Nucleic Acids) III (Recombinant DNA Technology)", p. 233 (Susumu Hirose), Tokyo Kagaku Dozin (1992); R. Wu, L. Grossman, ed., "Methods in Enzymology", Vol. 154, p. 350 & p. 367, Academic Press, New York (1987); R. Wu, L. Grossman, ed., "Methods in Enzymology", Vol. 100, p. 457 & p. 468, Academic Press, New York (1983); J. A. Wells et al., Gene, 34: 315, 1985; T. Grundstroem et al., Nucleic Acids Res., 13: 3305, 1985; J. Taylor et al., Nucleic Acids Res., 13: 8765, 1985; R. Wu, ed., "Methods in Enzymology", Vol. 155, p. 568, Academic Press, New York (1987); and A. R. Oliphant et al., Gene, 44: 177, 1986. For example, there may be mentioned such methods as site-directed mutagenesis (site-specific mutagenesis) using a synthetic oligonucleotide (Zoller et al., Nucl. Acids Res., 10: 6487, 1987; Carter et al., Nucl. Acids Res., 13: 4331, 1986), cassette mutagenesis (Wells et al., Gene, 34: 315, 1985), restriction selection mutagenesis (Wells et al., Philos. Trans. R. Soc. London Ser. A, 317: 415, 1986), alanine scanning (Cunningham & Wells, Science, 244: 1081-1086, 1989), PCR mutagenesis, Kunkel method, dNTP[αS] method (Eckstein), and region-directed mutagenesis using sulfurous acid or nitrous acid.

In producing by the gene recombination technology, it is also possible to cause expression of the desired protein in the form of a fused protein. The fused protein thus obtained can be purified by affinity chromatography, for instance, utilizing the fused portion thereof. As such fused protein, there may be mentioned one fused to histidine tag, or to β-galactosidase (β-gal), maltose-binding protein (MBP), glutathione-S-transferase (GST), thioredoxin (TRX) or Cre recombinase amino acid sequence. Similarly, it is also possible to add a heterogeneous epitope tag to the polypeptide for enabling purification by immunoaffinity chromatography using an antibody specifically binding to the epitope. As the epitope tag to be used in a more suited embodiment, there may be mentioned, for example, AU5, c-Myc, CruzTag 09, CruzTag 22, CruzTag 41, Glu-Glu, HA, HA.11, KT3, FLAG (registered trademark; Sigma-Aldrich), Omni-probe, S-probe, T7, Lex A, V5, VP16, GAL4, and VSV-G (e.g. Field et al., Molecular and Cellular Biology, 8: pp. 2159-2165 (1988); Evan et al., Molecular and Cellular Biology, 5: pp. 3610-3616 (1985); Paborsky et al., Protein Engineering, 3 (6): pp. 547-553 (1990); Hopp et al., BioTechnlogy, 6: pp. 1204-1210 (1988); Martin et al., Science, 255: pp. 192-194 (1992); Skinner et al., J. Biol. Chem., 266: pp. 15163-15166 (1991); Lutz-Freyermuth et al., Proc. Natl. Acad. Sci. USA, 87: pp. 6393-6397 (1990)).

The two-hybrid method using a yeast can also be utilized. Further, the fused protein may be one resulting from addition of a marker to render the protein detectable. In a more preferred embodiment, the detectable marker may be Biotin Avi Tag of the biotin/streptavidin system, or a fluorescent substance, for instance. The fluorescent substance includes, among others, an *Aeguorea victorea*—or like fluorescent jellyfish-derived green fluorescent protein (GFP), variants thereof (GFP variants), for example EGFP (enhanced-humanized GFP), rsGFP (red-shift GFP), yellow fluorescent protein (YFP), green fluorescent protein (GFP), cyan fluorescent protein (CFP), blue fluorescent protein (BFP), and *Renilla reniformis*-derived GFP (Atsushi Miyawaki (ed.), Jikken Igaku (Experimental Medicine), an extra number, Posutogenomu Jidai no Jikken Koza (Experiments in Postgenomic Era) 3-GFP and Bioimaging, Yodosha (2000)). Detection can also be made using an antibody (including a monoclonal antibody and a fragment thereof) specifically recognizing the above-mentioned fused tag. The protein obtained (which may include a peptide or polypeptide) can be immobilized by biding the same to an appropriate carrier or solid phase by a known technique such as an enzyme immunoassay technique. The immobilized protein or immobilized peptide can conveniently be used in binding assays or screening of substances.

The protein obtained (which may include a peptide or polypeptide) can be used for screening purposes with its biological activity as an indicator. For example, it is possible to react the protein with a substrate of a known carboxylesterase, for example p-nitrophenylacetic acid, and assay cauxin by measuring the color developed by the decomposition product, since cauxin is considered to have carboxylesterase activity. Typically, for instance, a filter paper or the like is impregnated with an aqueous solution of p-nitrophenylacetic acid and then immersed in a feline urine sample for detecting a red color developed by the product formed upon decomposition by carboxylesterase activity.

It is evident that the cauxin gene codes for a novel polypeptide. Hence, recombinant plasmids constructed using the cauxin gene are all novel recombinants, and transformants or transfectants obtained by transformation or transfection with the plasmids are also novel.

In the present specification, the term "substantially equivalent" means that the activities of a protein, for example its enzyme activity, physiological activity and biological activity, are substantially the same as those of another protein. The term also includes, within the meaning thereof, the case where a protein has an activity of substantially the same nature as compared with another. As the activity of substantially the same nature, there may be mentioned, for example, carboxylesterase activity, activity serving as a marker for feline nephropathy, for example glomerulopathy or interstitial lesion, and decomposing activity against synthetic substrates of carboxylesterases. The activities of substantially the same nature indicate that the activities are each qualitatively of the same nature, for example physiologically, pharmacologically or biologically, as compared with the counterpart. For example, it is preferred that the activities, such as cauxin activity and carboxylesterase activity, be equivalent (about 0.1 to about 10 times). However, the levels of these activities, the molecular weight of the protein and other quantitative factors may differ.

For synthesizing the protein of the present invention and partial peptides thereof, methods known in the field of peptide synthesis, for example liquid phase, solid phase and like chemical methods of synthesis, can be used. According to such methods, a resin for protein or peptide synthesis, for instance, is used, and adequately protected amino acids are subjected to condensation one by one on the resin according to the desired amino acid sequence by any of various per se known condensation methods. In the condensation reaction, various per se known activating reagents are preferably used. Preferred as such reagents are carbodiimides such as dicyclohexylcarbodiimide. When the product has a protective group(s), deprotection is carried out in an appropriate manner to give the desired product.

The protein of the present invention and partial peptides thereof, when obtained in the free form, may be converted to salts by a per se known method or a modification thereof and, when obtained in a salt form, may be converted to the free form or to other salts by a per se known method or a modification thereof. The salts of the protein of the present invention and partial peptides thereof preferably include, but are not limited to, physiologically acceptable ones or pharmaceutically acceptable ones. Such salts may include salts with inorganic acids such as hydrochloric acid, hydrobromic acid, sulfuric acid, nitric acid and phosphoric acid, and salts with organic acids such as acetic acid, formic acid, maleic acid, fumaric acid, succinic acid, citric acid, tartaric acid, malic acid, benzoic acid, methanesulfonic acid, p-toluenesulfonic acid and benzene sulfonic acid. The salts may further include ammonium salts, salts with organic nucleotide bases such as ethylamine, dimethylamine, trimethylamine and hydroxylamine, and so on.

In an embodiment, the feline nephropathy diagnosing agent of the present invention contains an anti-cauxin antibody as an active component. The anti-cauxin antibody can be obtained as a polyclonal or monoclonal antibody by per se known means.

In the present specification, the term "antibody" may be used in a broad sense. Thus, it includes individual monoclonal antibodies to the desired cauxin polypeptide and related peptide fragments, and antibody compositions having specificity for various epitopes. It includes univalent antibodies and polyvalent antibodies as well as monoclonal antibodies and polyclonal antibodies and, further, the native (intact) molecules, and fragments and derivatives thereof. Thus, it includes such fragments as F(ab')$_2$, Fab' and Fab and, further, chimera antibodies or hybrid antibodies having at least two antigen or epitope binding sites, or bispecific recombinant antibodies such as quadromes and triomes, interspecific hybrid antibodies, anti-idiotype antibodies and, further, chemically modified or processed ones which can be considered to be derivatives of these, antibodies obtained by applying a per se known cell fusion or hybridoma technology or antibody engineering technology or utilizing a synthetic or semisynthetic technology, antibodies prepared by applying a prior art technology known from the antibody formation viewpoint or using a recombinant DNA technology, and antibodies having neutralizing activity or binding activity against the target antigen substance or target epitope as described and defined herein.

A particularly preferred antibody according to the present invention can specifically recognize the native type cauxin polypeptide. For obtaining the anti-cauxin antibody as a polyclonal antibody, a mammal or bird, for instance, is immunized with the immunogen cauxin or a fragment thereof, or a partial peptide of the cauxin sequence, and antiserum is collected from the mammal or bird. The polyclonal antibody contained in this antiserum can then be used. The mammal to be immunized with this sensitizing antigen cauxin is not particularly restricted but, generally, rodents such as mice, rats, and hamsters and, further, rabbits, sheep, goats, cattle, horses, pigs, dogs, monkeys and other primates, and birds such as chickens are used. In some cases, it is preferred that the mammal be selected considering the compatibility with the parent cells to be used in cell fusion.

The immunization of animals with the sensitizing antigen is carried out by a per se known method. For example, a method in general use comprises intraperitoneally or subcutaneously injecting the sensitizing antigen into the mammals or the like. In immunization with the sensitizing antigen, an appropriate carrier may be used. After a predetermined period of feeding of the immunized animals, the polyclonal antibody-containing antiserum can be prepared from the blood collected from each of the animals. After confirming that it specifically recognizes cauxin, the antiserum obtained is submitted to use as a diagnostic agent for feline nephropathy.

Cauxin, which is to be used as the sensitizing antigen for antibody production, can be obtained by causing expression of the cauxin gene/amino acid sequence disclosed herein.

In the practice of the present invention, the anti-cauxin antibody may also be one obtained as a mammal-derived monoclonal antibody.

The monoclonal antibody produced against the antigenic substance can be produced by any of the methods capable of causing the production of antibody molecules in a series of cell lines under cultivation. The modifier "monoclonal" indicates the characteristic of an antibody that it belongs to a substantially homogeneous antibody population. It is not to be construed that the antibody should be produced by a certain specific method. Individual monoclonal antibodies each includes a population of the same antibodies except that a slight amount of a mutant(s) possible formed spontaneously may be present therein. Monoclonal antibodies each has high specificity and is directed to one single antigenic site. As compared with ordinary (polyclonal) antibody preparations typically containing various antibody species directed to different antigenic determinants (epitopes), each monoclonal antibody is directed to one single antigenic determinant on the antigen. In addition to their specificity, monoclonal antibodies are synthesized by hybridoma culture and are superior in that they are not or only a little contaminated with other immunoglobulins. The monoclonal antibodies include hybrid antibodies and recombinant antibodies. So long as they show the desired biological activities, a constant region domain may be substituted for a variable region domain thereof, or a heavy chain may be substituted for a light chain thereof, a chain derived from a certain species may be replaced with a chain derived from another species, or they may be fused with a heterogeneous protein, irrespective of their origin or immunoglobulin class or subclass (e.g. U.S. Pat. No. 4,816,567; Monoclonal Antibody Production Techniques and Applications, pp. 79-97, Marcel Dekker, Inc., New York, 1987).

As preferred examples of the monoclonal antibody production, there may be mentioned the hybridoma method (G. Kohler and C. Milstein, Nature, 256, pp. 495-497 (1975)); human B cell hybridoma method (Kozbor et al., Immunology Today, 4, pp. 72-79 (1983); Kozbor, J. Immunol., 133, pp. 3001 (1984); Brodeur et al., Monoclonal Antibody Production Techniques and Applications, pp. 51-63, Marcel Dekker, Inc., New York (1987)); trioma method; EBV-hybridoma method (Cole et al., Monoclonal Antibodies and Cancer Therapy, Alan R. Liss, Inc., pp. 77-96 (1985)) (methods of producing monoclonal antibodies); U.S. Pat. No. 4,946,778 (technology of producing single-chain antibodies) and, further, the following references may be cited: S. Biocca et al., EMBO J, 9, pp. 101-108 (1990); R. E. Bird et al., Science, 242, pp. 423-426 (1988); M. A. Boss et al., Nucl. Acids Res., 12, pp. 3791-3806 (1984); J. Bukovsky et al., Hybridoma, 6, pp. 219-228 (1987); M. DAINO et al., Anal. Biochem., 166, pp. 223-229 (1987); J. S. Huston et al., Proc. Natl. Acad. Sci. USA, 85, pp. 5879-5883 (1988); P. T. Jones et al., Nature, 321, pp. 522-525 (1986); J. J. Langone et al. (ed.), "Methods in Enzymology", Vol. 121 (Immunological Techniques, Part I: Hybridoma Technology and Monoclonal Antibodies), Academic Press, New York (1986); S. Morrison et al., Proc. Natl. Acad. Sci. USA, 81, pp. 6851-6855 (1984); V. T. Oi et al., BioTechniques, 4, pp. 214-221 (1986); L. Riechmann et al., Nature, 332, pp. 323-327 (1988); A. Tramontano et al., Proc. Natl. Acad. Sci. USA, 83, pp. 6736-6740 (1986); C. Wood et al., Nature, 314, pp. 446-449 (1985); Nature 314, pp. 452-454 (1985); and references cited therein (the descriptions therein are incorporated herein by reference).

The monoclonal antibody according to the present invention includes "chimera" antibodies (immunoglobulins), in particular, in which part of the heavy chain and/or light chain has a sequence identical or homologous to the corresponding sequence of an antibody derived from a specific species or belonging to a specific antibody class or subclass while the remaining portions are identical or homologous to the corresponding sequences of an antibody derived from another species or belonging to another antibody class or subclass, so long as they show the desired biological activities (U.S. Pat. No. 4,816,567; Morrison et al., Proc. Natl. Acad. Sci. USA, 81, pp. 6851-6855 (1984)).

The monoclonal antibody according to the present invention includes those produced by mammal-derived hybridomas, and those produced by hosts transformed with an expression vector containing the antibody gene utilizing the genetic engineering technology.

Monoclonal antibody-producing hybridomas capable of producing anti-cauxin antibodies can be prepared by utilizing the cell fusion technology using myeloma cells, as follows. Thus, they can be prepared by carrying out immunization with a conventional method using cauxin or a fragment thereof as a sensitizing antigen, fusing the immunized cells obtained with per se known parent cells by a conventional cell fusion method, and screening for monoclonal antibody-producing cells by a conventional screening method.

As for the method of preparing cauxin or a fragment thereof and the method of immunizing mammals, among others, the techniques mentioned above for the preparation of polyclonal antibody-containing antisera can be employed. In this case, when mammals, in particular, are immunized, immunized cells are collected from the mammals after confirming an increase in the serum level of the desired antibody, and they are subjected to cell fusion. Spleen cells, in particular, are preferred as the immunized cells.

Mammalian myeloma cells are used as counterpart parent cells to be fused with the above immunized cells. Various known cell lines can be used as the myeloma cells. The cell fusion between the immunized cells and myeloma cells and other steps can be carried out basically by known methods, for example by the method of Kohler and Milstein (Kohler, G. and Milstein, C., Methods Enzymol. (1981), 73, 3-46).

In the following, the production of antibodies is described in detail, taking monoclonal antibodies as an example. The antibody of the present invention may be a monoclonal antibody obtained by utilizing the cell fusion technology using myeloma cells. It can be produced via the following steps, for instance. (1) Preparation of an immunogenic antigen, (2) immunization of an animal with the immunogenic antigen, (3) preparation of myeloma cells, (4) cell fusion between antibody producing cells and myeloma cells, (5) selection of hybridomas (fused cells) and cloning, and (6) monoclonal antibody production.

(1) The immunogenic antigen can be prepared in the following manner. While, as mentioned above, the native type cauxin polypeptide or a fragment derived therefrom (which may include parts of domain polypeptide, fragments, partial peptides and synthetic peptides and which may be a recombinant cauxin polypeptide) may be used as the antigen, it is also possible to use, as the antigen, an appropriate oligopeptide chemically synthesized based on the information about the amino acid sequence of cauxin as determined. As typical examples, there may be mentioned peptides comprising at least five consecutive amino acid residues occurring in the region selected from the group consisting of (1) the amino acid sequence shown under SEQ ID NO: 2 in the sequence listing or the amino acid sequence of a partial domain(s) thereof (2) the amino acid sequence constituting the C terminal side domain out of the sequence shown under SEQ ID NO: 2 or a partial fragment thereof or (3) the amino acid sequence constituting the N terminal side domain out of the sequence shown under SEQ ID NO: 2 out of the sequence shown under SEQ ID NO: 2 in the sequence listing or a partial fragment thereof.

The antigen as such may be used in admixture with an appropriate adjuvant for immunizing an animal, or may be used in the form of an immunogenic conjugate. The antigen to be used as the immunogen may be one derived from cauxin by fragmentation or a synthetic polypeptide fragment obtained by chemical synthesis following polypeptide designing by selecting a characteristic sequence region based on the amino acid sequence of cauxin. It is also possible to bind that fragment to various carrier proteins via an appropriate condensing agent to give immunogenic conjugates such as hapten-protein conjugates and design monoclonal antibodies capable of reacting with specific sequences alone (or recognizing specific sequences alone) using such conjugates. A cysteine residue, for instance, may be added in advance to the polypeptide designed to thereby facilitate the preparation of immunogenic conjugates. In binding to carrier proteins, the carrier proteins can be first activated. For such activation, an activating binding group is introduced. The activating binding group includes (1) activated ester or activating carboxyl groups, such as nitrophenyl ester, pentafluorophenyl ester, 1-benzotriazole ester, and N-succinimide ester groups, and (2) activating dithio groups, such as 2-pyridyldithio and like groups. The carrier proteins may include among others, keyhole lympet hemocyanin (KLH), bovine serum albumin (BSA), egg albumin, globulin, polypeptides such as polylysine, and bacterial cell components, for example BCG.

(2) Animals can be immunized with the immunogenic antigen in the following manner. The immunization can be carried out by any of the methods known to those skilled in the art, for example according to the methods described in Shigeru Muramatsu et al. (ed.), Jikken Seibutsugaku Koza (Lectures on Experimental Biology) 14, Immunobiology, Maruzen, 1985; Japanese Biochemical Society (ed.), Zoku Seikagaku Jikken Koza (Experiments in Biochemistry, Second Series) 5, Men'eki Seikagaku Kenkyuho (Study Methods in Immunobiochemistry, Tokyo Kagaku Dozin, 1986; Japanese Biochemical Society (ed.), Shin Seikagaku Jikken Koza (Experiments in Biochemistry, Updated) 12, Molecular Immunology III, Antigens, Antibodies, and Complements, Tokyo Kagaku Dozin, 1992; and so on. Immunization can be attained by injecting the immunizing agent (if necessary together with an adjuvant) once or more times into mammals. Typically, the immunizing agent is subcutaneously or intraperitoneally injected, alone or together with an adjuvant, into mammals a plurality of times. The immunizing agent includes the above-mentioned antigen peptides or peptide fragments related thereto. The immunizing agent may be used in the form of a conjugate with a protein (e.g. one of the above-mentioned carrier proteins) known to be antigenic in the mammals to be treated for immunization. The adjuvant includes, among others, Freund's complete adjuvant, Ribi adjuvant pertussis vaccine, BCG, lipid A, liposomes, aluminum hydroxide, and silica. The immunization is carried out using, for example, BALB/c and other mice, hamsters, or other appropriate animals. The dose of the antigen is about 1 to 400 µg/animal in mice, for instance, and the antigen is generally injected intraperitoneally or subcutaneously into the host animals and, thereafter, boosters are repeated about 2 to 10 times at intervals of 1 to 4 weeks, preferably 1 to 2 weeks, by the intraperitoneal, subcutaneous, intravenous or intramuscular route. Not only BALB/c mice but also F1 mice from BALB/c mice and mice of another strain may be used as the mice to be subjected to immunization. If necessary, an antibody titer measuring system may be constructed 'so that the extent of immunization of animals can be confirmed by antibody titer measurements. The antibody of the present invention may be one obtained from an animal immunized in the above manner, including an antiserum, polyclonal antibody, etc.

(3) Myeloma cells can be prepared in the following manner. The immortally growing strain (tumor cell strain) to be used in cell fusion can be selected from among cell strains incapable of producing immunoglobulins, for example P3-NS-1-Ag4-1 (NS-1, Eur. J. Immunol., 6: 511-519, 1976), SP-2/0-Ag14 (SP-2, Nature, 276: 269-270, 1978), mouse myeloma MOPC-21 cell line-derived P3-X63-Ag8-U1 (P3U1, Curr. Topics Microbiol. Immunol., 81: 1-7, 1978), P3-X63-Ag8 (X63, J. Immunol., 81: 495-497, 1975), P3-X63-Ag8-653 (653, J. Immunol 123: 1548-1550, 1979) and the like. 8-Azaguanine-resistant mouse myeloma cell strains are subcultured on a cell culture medium, such as Dulbecco's MEM (DMEM) or RPMI-1640 medium, supplemented with an antibiotic, such as penicillin or amikacin, fetal calf serum (FCS) and the like, and further supplemented with 8-azaguanine (e.g. 5 to 45 µg/ml). A necessary number of cells can be prepared by subculturing on a normal medium 2 to 5 days before cell fusion. The cell strain to be used may also be prepared by completely thawing the cryopreserved cell strain at about 37° C., washing three or more times with a normal medium, such as RPMI-1640 medium, and cultivating on a normal medium until a required number of cells are obtained.

(4) The cell fusion between antibody-producing cells and myeloma cells can be carried out in the following manner. The spleen of an animal, for example a mouse, immunized in the above step (2) is excised 2 to 5 days after the final immunization, and a spleen cell suspension is prepared therefrom. In addition to spleen cells, lymph node cells obtained from various sites of the organism may also be used for cell fusion. More specifically, the cell fusion is carried out, for example, in an ordinary nutrient culture fluid in the presence of a cell fusion promoter. Usable as the culture fluid in the above cell fusion are such media favorable for the growth of the above-mentioned myeloma cells as RPMI 1640 culture fluid and MEM culture fluid, and culture fluids commonly used in this kind of cell culture. Auxiliary serum such as fetal calf serum (FCS) may further be used combinedly. The thus-obtained spleen cell suspension and the myeloma cell line obtained in the above step (3) are placed in a cell culture medium, such as minimum essential medium (MEM), DMEM or RPMI-1640 medium, and a cell fusion promoter, for example polyethylene glycol, is added. The cell fusion promoter may be any of those known in this field of art, and inactivated Sendai virus (HVJ; hemagglutinating virus of Japan) and the like may also be mentioned as such.

Preferably, 0.5 to 2 ml of 30 to 60% polyethylene glycol can be added, polyethylene glycol species having a molecular weight of 1,000 to 8,000 can be used, and polyethylene glycol species having a molecular weight of 1,000 to 4,000 are more preferably used. The concentration of polyethylene glycol in the fusion medium is preferably 30 to 60%, for instance. If necessary, a small amount of such an auxiliary as dimethyl sulfoxide may be added to thereby increase the fusion efficiency. The mixing ratio between immunocytes and myeloma cells, namely the ratio spleen cells (lymphocytes):myeloma cells to be used for fusion, may be selected arbitrarily and, for example, may be 1:1 to 20:1, more preferably 4:1 to 10:1.

In cell fusion, the immunized cells and myeloma cells, in a predetermined mixing ratio, are thoroughly blended in the culture fluid, and a PEG solution (e.g. with an average molecular weight of about 1,000 to 6,000) warmed at about 37° C. is added generally to a concentration of 30 to 60% (w/v), and the mixture is stirred, whereby the desired fused cells (hybridomas) are formed. Then, the procedure comprising adding an appropriate culture fluid and removing the supernatant by centrifugation is repeated to thereby remove the cell fusion agent and other components unfavorable for the growth of hybridomas.

The fusion reaction is carried out for 1 to 10 minutes and, then, a cell culture medium such as RPMI-1640 medium is added. It is also possible to repeat the fusion treatment a plurality of times. After the fusion treatment, cells are separated by centrifugation and then transferred to a selective medium.

(5) Hybridomas (fused cells) can be selected and cloned in the following manner. The selective medium may include conventional selective culture fluids, such as FCS-containing MEM, RPMI-1640 medium or like media containing hypoxanthine, aminopterine and thymidine, namely the so-called HAT media. In such a HAT medium as mentioned above, the cultivation is continued for a period (generally several days to several weeks) sufficient for other cells (unfused cells) than the desired hybridomas to die out. A method of selective medium exchange generally comprises adding, on the next day, a volume equal to the volume of the portion distributed onto the culture plate and thereafter replacing a half of that volume with a fresh portion of the HAT medium at intervals of 1 to 3 days. Appropriate modifications of this method may also be used. On the 8th to 16th days after fusion, the medium exchange may be conducted with the so-called HT medium, which is free of aminopterine, at intervals of 1 to 4 days. Mouse thymocytes, for instance, may be used as feeder cells, and this is preferred in some instances.

Screening is performed by assaying, for the desired antibody, the culture supernatant in a well in which a vigorous hybridoma growth is seen in a measuring system for radioimmunoassay (RIA), enzyme immunoassay (ELISA), fluorescent immunoassay (FIA), luminescent immunoassay (LIA) or western blotting, for instance, or a fluorescence-activated cell sorter (FACS), using the predetermined fragment peptide as an antigen or using a labeled anti-mouse antibody. The hybridomas producing the desired antibody are subjected to cloning. The cloning can be carried out by picking up colonies in agar medium or by the limiting dilution method. The limiting dilution method is more preferred. The cloning is preferably repeated a plurality of times. The thus-produced monoclonal antibody producing hybridomas can be subcultured in an ordinary culture fluid and can be stored in liquid nitrogen for a long period of time.

(6) The monoclonal antibody production can be carried out in the following manner. For obtained a monoclonal antibody from the corresponding hybridomas, there may be employed, for example, a method comprising cultivating the hybridomas by a conventional method and recovering the monoclonal antibody as the culture supernatant, or a method comprising administering the hybridomas to a mammal compatible therewith and allowing them to grow and recovering the antibody as the ascitic fluid from the mammal. The former method is suited for obtaining a highly pure antibody, while the latter method is suited for mass production of an antibody.

Thus, by cultivating the hybridoma strain obtained in an appropriate growth medium, such as FCS-containing MEM or RPMI-1640 medium, it is possible to obtained the desired monoclonal antibody from the culture supernatant. For obtained the antibody in large quantities, the method comprising allowing the hybridomas to grow in the ascitic fluid may be mentioned. In this case, hybridomas of each strain are transplanted into the peritoneal cavity of a histocompatible animal isogenic to the animal serving as the origin of myeloma cells and allowed to grow, or transplanted into a nude mouse, for instance, and allowed to grow. The monoclonal antibody produced in the ascitic fluid in the animal can then be recovered. Prior to hybridoma transplantation, the animal may be intraperitoneally administered with a mineral oil, such as pristane (2,6,10,14-tetramethylpentadecane). After hybridoma growth following this treatment, the ascitic fluid can be collected. The ascitic fluid may be used as the monoclonal antibody either as such or after purification by conventional methods, for example salting out by the ammonium sulfate precipitation, for instance, gel filtration using Sephadex, ion exchange chromatography, electrophoresis, dialysis, ultrafiltration, affinity chromatography, high-performance liquid chromatography and/or the like. Preferably, the monoclonal antibody-containing ascitic fluid can be purified and isolated by ammonium sulfate fractionation, followed by treatment with an anion exchange gel, such as DEAE-Sepharose, and an affinity column, such as a protein A column. Especially preferred are affinity chromatography with an immobilized antigen or antigen fragment (e.g. synthetic peptide, recombinant antigen protein or peptide, site specifically recognized by the antigen) column, affinity chromatography with an immobilized protein A column, and hydroxyapatite chromatography, among others.

Further, transgenic mice or other organisms, for example other mammals, can be used in causing expression of antibodies to the immunogen polypeptide product of the present invention.

It is also possible to determine the sequences of the antibodies thus obtained in large quantities and/or produce antibodies by the gene recombination technology utilizing the nucleic acid sequence coding for the antibody obtained from a hybridoma strain. The nucleic acid coding for the monoclonal antibody can be isolated for sequencing by a conventional method, for example by using an oligonucleotide probe capable of specifically binding to the gene coding for the heavy chain or light chain of the mouse antibody. Once isolated, the DNA can be inserted into an expression vector for introduction into CHO, COS or like host cells. The DNA can be modified, for example, by substituting a sequence coding for a feline heavy chain or light chain constant region domain for the homogeneous murine sequence (Morrison et al., Proc. Natl. Acad. Sci. USA, 81: 6581, 1984). Thus, it is possible to prepare a chimera antibody or hybrid antibody having the desired binding specificity. It is also possible to modify the antibody by applying a technology of chemical protein synthesis, including the use of such a condensing agent as mentioned below, to give a chimera antibody or hybrid antibody.

Further, such antibody fragments as Fab, Fab' and F(ab')$_2$ obtained by treatment of those antibodies with an enzyme such as trypsin, papain or pepsin, if necessary followed by reduction may also be used.

The antibodies can be used in any of the known assay methods, for example competitive binding assay, direct and indirect sandwich assay, and immunoprecipitation (Zola, Monoclonal Antibodies: A Manual of Techniques, pp. 147-158 (CRC Press, Inc. 1987)). For conjugating the antibodies to a detectable atomic group, any of the methods known in the relevant field can be used and, thus, for example, mention may be made of the methods described in David et al., Biochemistry, Vol. 13, pp. 1014-1021 (1974); Pain et al., J. Immunol. Meth., 40: pp. 219-231 (1981); and "Methods in Enzymology", Vol. 184, pp. 138-163 (1990). Usable as the antibody to be labeled are an IgG fraction and, further, the specific binding portion Fab' obtainable by reduction following pepsin digestion. In these cases, the label includes enzymes (peroxidase, alkaline phosphatase or β-D-galactosidase, etc.), chemical substances, fluorescent substances and radioisotopes, among others.

The detection and assay in the practice of the present invention can be performed by immunostaining, for example tissue or cell staining, immune electron microscopy, immunochromatography, or immunoassay, for example competitive immunoassay or noncompetitive immunoassay, and radioimmunoassay (RIA), FIA, LIA, EIA, ELISA and the like may also be used. B-F separation may be made, or assaying can be made without such separation. Preferred are RIA, EIA, FIA, LIA and, further, sandwich assay. In sandwich assay, for instance, the anti-cauxin polypeptide antibody of the present invention or the antibody to a cauxin-related peptide fragment is used as one antibody, and the antibody to the C-terminal side residues of cauxin as the other, and one of them is labeled for rendering the same detectable (of course, other combinations are also possible and appropriate designing can be made according to the intended purpose). The other antibody capable of recognizing the same antigen is immobilized on a solid phase. The sample, labeled antibody and immobilized antibody are subjected to incubation treatment according to need for the successive reactions and, after separating the unbound antibodies, the label is assayed. The quantity of the label as assayed is proportional to the quantity of the antigen, namely the cauxin polypeptide antigen. This assay is called simultaneous sandwich assay, forward sandwich assay or reversed sandwich assay according to the order of addition of the immobilized antibody and labeled antibody.

Washing, stirring, shaking, filtration and/or preliminary antigen extraction, for instance, may suitably be employed in the process of assaying under specific conditions. Other assaying conditions such as specific reagents, concentrations of buffer solutions and the like, temperature and incubation treatment time can be varied according to the antigen concentration in the specimen, the nature of the test sample and other factors. The one skilled in the art will be able to carry out assaying by appropriately selecting optimum and effective conditions for each assay while using an ordinary method of experiment.

A large number of carriers are known for immobilizing antigens or antibodies and, appropriate ones may be selected from among them for use in the practice of the present invention. Various carriers are known to be useful in antigen-antibody and like reactions and, of course, appropriate ones can be used for use in the practice of the present invention. Especially preferred for use are glass, for example activated glass such as aminoalkylsilylated glass, porous glass, silica gel, silica-alumina, alumina, magnetized iron, magnetized alloys and other inorganic materials, polyethylene, polypropylene, polyvinyl chloride, polyvinylidene fluoride, polyvinyl polymers, polyvinyl acetate, polycarbonates, polymethacrylates, polystyrene, styrene-butadiene copolymers, polyacrylamide, crosslinked polyacrylamide, styrene-methacrylate copolymers, polyglycidyl methacrylate, acrolein-ethylene glycol dimethacrylate copolymers and the like, crosslinked albumin, collagen, gelatin, dextran, agarose, crosslinked agarose, cellulose, microcrystalline cellulose, carboxylmethylcellulose, cellulose acetate and other natural or modified cellulose, crosslinked dextran, nylons and other polyamides, polyurethanes, polyepoxy resins and other organic polymers, such polymers obtained by emulsion polymerization, silicone rubbers and the like, cells, erythrocytes and the like. If necessary, they may have a functional group introduced therein using a silane coupling agent, for instance.

Furthermore, there may be mentioned filter paper, beads, tubes, cuvettes, inside walls of test vessels such as test tubes, titer plates, titer wells, microplates, glass cells, synthetic resin cells and cells made of some other synthetic material, and the surfaces of solid substances (bodies) such as glass rods, rods made of a synthetic material, rods having a thickened or tapered end, rods having a round projection or flat projection at an end, and thin plate-like rods.

Antibodies can be bound to these carriers and, preferably, the anti-cauxin antibody (inclusive of antiserum or purified antibody) or anti-cauxin monoclonal antibody specifically reacting with the antigen obtained in accordance with the present invention can be bound to those carriers. The binding of the carrier with these components to be involved in the antigen-antibody reaction can be realized by physical means such as adsorption, by chemical means using a condensing agent or an activated form, or by means utilizing a mutual chemical binding reaction, for instance. As the label, there may be mentioned enzymes, enzyme substrates, enzyme inhibitors, prosthetic groups, coenzymes, enzyme precursors, apoenzymes, fluorescent substances, chromophores, chemoluminescent compounds, luminescent substances, chromogens, magnetic substances, metal particles, for example gold colloid, nonmetallic element particles, for example selenium colloid, radioactive substances, and so forth. The enzymes include dehydrogenases, reductases, oxidases and other oxidation-reduction enzymes, transferases catalyzing the transfer of an amino, carboxyl, methyl, acyl or phosphoryl group, for instance, hydrolases hydrolyzing the ester, glycoside, ether or peptide bond, for instance, lyases, isomerases, ligases and so on. A plurality of enzymes may be utilized in combination for detection purposes.

Enzymatic cycling, for instance, may also be utilized. As the isotope labels of typical radioactive substances, there may be mentioned [$^{32}$P], [$^{125}$I], [$^{131}$I], [$^{3}$H], [$^{14}$C], [$^{35}$S] and so forth. As typical enzyme labels, there may be mentioned horseradish peroxidase and other peroxidases, *Escherichia coli*-derived β-D-galactosidase and other galactosidases, malate dehydrogenase, glucose-6-phosphate dehydrogenase, glucose oxidase, glucoamylase, acetylcholine esterase, catalase, bovine small intestine-derived alkaline phosphatase, *Escherichia coli*-derived alkaline phosphatase and other alkaline phosphatases, among others. When alkaline phosphatase is used, assaying can be made using an umbelliferone derivative such as 4-methylumbelliferyl phosphate, a phosphorylated phenol derivative such as nitrophenyl phosphate, an enzymatic cycling system utilizing NADP, a luciferin derivative, a dioxetane derivative or a like substrate and measuring the resulting fluorescence or chemiluminescence. A luciferin-luciferase system may also be utilized. When catalase is used, oxygen is formed upon reaction with hydrogen peroxide and that oxygen can also be detected by means of an electrode, for instance. The electrode may be a glass electrode, an ion-selective electrode with a hardly soluble salt membrane, a liquid-membrane electrode or a polymer membrane electrode, for instance.

A biotin label and an enzyme-labeled avidin (streptavidin) may be substituted for the enzyme label. Thus, it is possible to suitably employ a sensitivity increasing method known in the art, for example the use of such a biotin-avidin system or the use of a secondary antibody such as an antibody to anti-galectin antibody. It is also possible to use a plurality of different labels. In such case, is also becomes possible to carry out a plurality of measurements continuously or discontinuously, and simultaneously or separately. In the practice of the present invention, enzyme-reagent combinations may also be utilized for the formation of signals, for example the combinations of 4-hydroxyphenylacetic acid, o-phenylenediamine (OPD), tetramethylbenzidine (TMB); 5-aminosalicylic acid, 3,3-diaminobenzidine tetrahydrochloride (DAB), 3-amino-9-ethylcarbazole (AEC), tyramine, lucigenin, luciferin and derivatives thereof, Pholad luciferin and the like with horseradish peroxidase, the combinations of Lumigen PPD, (4-methyl)umbelliferyl phosphate, p-nitrophenol phosphate, phenol phosphate, bromochloroindolyl phosphate (BCIP), AMPAK™ (DAKO), AmpliQ™ (DAKO) and the like with alkaline phosphatase, the combinations of 4-methylumbelliferyl-β-D-galactoside or like umbelliferyl galactosides, o-nitrophenyl-β-D-galactoside or like nitrophenyl galactosides and the like with β-D-galactosidase or glucose-6-phosphate dehydrogenase, and the combination of ABTS with glucose oxidase, and use can be made of those compounds which can form hydroquinone, hydroxybenzoquinone, hydroxyanthraquinone and like quinol compounds, lipoic acid, glutathione and like thiol compounds, phenol derivatives, ferrocene derivatives and the like under the action of enzymes or the like.

The fluorescent substances or chemiluminescent compounds include fluorescein isothiocyanate (FITC), rhodamine derivatives such as rhodamine B isothiocyanate, tetramethylrhodamine isothiocyanate (RITC) and tetramethylrhodamine isothiocyanate isomer R (TRITC), 7-amino-4-coumarin-3-acetic acid, dansyl chloride, dansyl fluoride, fluorescamine, phycobilin protein, acridinium salts, luciferin, luciferase, aequorin and like luminols, imidazole, oxalate esters, rare earth chelate compounds, and coumarin derivatives, among others. For detecting the resulting signals, inclusive of chemiluminescence and fluorescence, or the like, visual observation may be employed, or a per se known apparatus may also be used; thus, for example, a fluorophotometer or a plate reader may be used. For detecting the signal emitted by a radioisotope, for instance, a per se known apparatus may be used; for example, a gamma counter or scintillation counter or the like may also be used.

The labeling can be carried out utilizing the reaction between a thiol group and a maleimide group, the reaction between a pyridyl disulfide group and a thiol group or the reaction between an amino group and an aldehyde group, for instance, and an appropriate method can be selected from among the known methods, methods obvious to those skilled in the art and, further, modifications thereof.

Further, condensing agents which can be used in preparing the above-mentioned immunogenic conjugates and condensing agents which can be used in binding to carriers, and the like can be used. Such condensing agents include, among others, formaldehyde, glutaraldehyde, hexamethylene diisocyanate, hexamethylene diisothiocyanate, N,N'-polymethylenebis-iodoacetamide, N,N'-ethylenebismaleimide, ethylene glycol bissuccinimidyl succinate, bisdiazobenzidine, 1-ethyl-3-(3-dimethylaminopropyl)carbodiimide, succinimidyl 3-(2-pyridyldithio)propionate (SPDP), N-succinimidyl 4-(N-maleimiidomethyl)cyclohexane-1-carboxylate (SMCC), N-sulfosuccinimidyl 4-(N-maleimidomethyl)cyclohexane-1-carboxylate, N-succinimidyl (4-iodoacetyl) aminobenzoate, N-succinimidyl 4-(1-maleimidophenyl)butyrate, N-($\epsilon$-maleimidocaproyloxy)succinimide (EMCS), iminothiolane, S-acetylmercaptosuccinic acid anhydride, methyl 3-(4'-dithiopyridyl)propionimidate, methyl 4-mercaptobutyrylimidate, methyl 3-mercaptopropionimidate, N-succinimidyl S-acetylmercaptoacetate, etc.

According to the assay method of the present invention, a substance to be assayed can be reacted successively or simultaneously With a labeled antibody reagent such as an antiserum, purified antibody or monoclonal antibody labeled with an enzyme or the like, and an antibody bound to a carrier. The order of addition of the reagents may vary according to the type of the carrier system selected. When a sensitized plastic bead or like bead is used, the assay can be performed by first placing the labeled antibody reagent such as a labeled antiserum, purified antibody or monoclonal antibody, together with a test sample containing a substance to be assayed, in an appropriate test tube, and then adding the sensitized plastic or like bead.

In the assay method of the present invention, an immunological assay method is used and, on that occasion, the solid carrier to be used can be arbitrarily selected from among various carriers differing in material and shape, for example balls, microplates, sticks, minute particles and test tubes made of a material on which proteins such as antibodies can be readily adsorbed, for example polystyrene, a polycarbonate, polypropylene or a polyvinyl.

The assay can be carried out in an appropriate buffer solution system so that an optimum pH, for example a pH of about 4 to about 9, can be maintained. Especially suited buffers are, for example, acetate, citrate, phosphate, Tris, triethanolamine; borate, glycine, carbonate, Tris-hydrochloride and veronal buffers. The buffers may be used in combination in an arbitrary mixing ratio. The antigen-antibody reaction is preferably carried out at a temperature between about 0° C. and about 60° C.

The incubation treatment of the antibody reagent such as an antiserum, purified antibody or monoclonal antibody labeled with an enzyme or the like, the antibody reagent bound to a carrier and, further, the substance to be assayed may be carried out until an equilibrium is arrived at. However the antigen-antibody reaction can be terminated, after restricted incubation treatment, by separating the solid phase from the liquid phase at a time by far earlier than the time when the reaction arrives at an equilibrium, and the extent of occurrence of the label such as an enzyme in the liquid phase or in the solid phase can be measured. The assay procedure can be performed using an automated measurement apparatus, and the indicator signal generated upon conversion of the substrate under the action of the enzyme can be detected and measured using a luminescence detector or photo detector or the like. In carrying out the antigen-antibody reaction, appropriate measures can be taken so that the reagents to be used, the substance to be assayed and, further the label such as an enzyme may be stabilized or the antigen-antibody reaction itself may be stabilized.

Further, a protein, a stabilizing agent, such a surfactant as mentioned below, a chelating agent and/or the like may be added to the incubation solution so that nonspecific reactions may be eliminated, inhibitory influences may be reduced and/or the assaying reaction may be activated. Ethylenediaminetetraacetate salts (EDTA) are more preferred as the chelating agent. The blocking treatment commonly employed in the relevant field or known to those skilled in the art may be carried out for preventing nonspecific binding reactions. Thus, for example, normal mammalian or other'sera or serum proteins, albumin, hemoglobin, ovalbumin (OVA), skimmed milk, milk fermentation substances, collagen, gelatin can be used for the treatment. So long as the purpose is to prevent nonspecific binding reactions, those methods can be used without any particular restriction. Further, the samples, solid phases and others can be washed with an appropriate solution selected from among the buffer solutions systems mentioned above and saline and, further, a surfactant selected from the group consisting of Tween 20 (trademark), Tween 80 (trademark), NP-40 (trademark), Triton X100 (trademark), Briji (trademark) and like nonionic surfactants, CHAPS and like amphoteric surfactants, cationic surfactants and anionic surfactants, among others, may be added to the solution.

The sample to be assayed according to the assay of the present invention includes various forms of solutions, colloidal solutions, nonfluid samples, etc. Preferred are, however, living body-derived samples, for example organs and tissues such as kidneys, urine, other body fluids, cell culture fluids, tissue culture fluids, tissue homogenates, biopsy samples, cells, and the like.

According to the present invention, a feline urinary protein testing kit in which an anti-cauxin antibody is used is preferably provided. The basic constitution of the kit may be similar to those of human pregnancy testing kits as disclosed in JP-A-H09-171019 and JP-A-H10-132817, for instance, and of simplified methods currently in general use. For example, the testing kit is a cauxin detection kit characterized in that it is composed of (a) a sample application site, (b) a labeled antibody-containing site, (c) an antigen detection site and (d) a reaction completion judging site, as disposed in that order on a carrier or support enabling substances to move in a wet condition, wherein (i) the labeled antibody-containing site contains a labeled anti-cauxin antibody (labeled antibody) which is capable of migrating on the carrier to the antigen detection site and then to the reaction completion judging site in a wet condition, (ii) an immobilized anti-cauxin antibody (immobilized antibody) is positioned on the detection site, and (iii) a site where an antibody (second antibody) to the antibody used as the labeled antibody is immobilized is formed on the reaction completion judging site, and wherein when a sample is applied to the sample application site, the sample is thus allowed to migrate on the carrier, elute the labeled antibody and pass through the immobilized antibody on the antigen detection site and through the second antibody site on the reaction completion judging site, for detecting cauxin in the sample, as well as the respective reagents to be used in the detection kit.

In a typical example, gold colloid immunochromatography, for instance, may be mentioned. The gold colloid immunochromatographic method comprises, for example, (1) preparing a gold colloid-labeled antibody by binding an appropriate amount of an anti-cauxin antibody to a gold colloid solution; (2) preparing an oblong strip-like filter paper on which a sample padding site for dropping a liquid sample, a gold colloid phase where the gold colloid-labeled antibody is positioned, a trapping site with the anti-cauxin antibody immobilized thereon, and an absorbent pad for absorbing the reaction mixture, with the four elements being disposed in line; and (3) dropping a cauxin-containing feline urine sample onto the sample pad, whereupon the sample migrates to the gold colloid phase owing to the chromatographic phenomenon and urinary cauxin is bound to the gold colloid-labeled antibody; (4) the gold colloid with cauxin bound to the surface thereof then further diffuses to the trapping site where the gold colloid is immobilized by the antibody on the trapping site; and (5) upon flocculation of the gold colloid on the trapping site, the site visually turns colored red purple. If cauxin is absent in the urine sample, the gold colloid passes through the trapping site and migrates to the absorbent pad, so that no coloration can be observed. When the urinary concentration of cauxin is high, the amount of the gold colloid flocculate increases, hence the coloration becomes intense (or the colored area extends). Thus, quantitative assaying becomes possible.

The carrier for enabling substances to migrate in a wet condition may be selected from among the carriers mentioned hereinabove, for example those known as porous carriers. The carrier can be prepared from an arbitrary material, such as a hygroscopic material, a porous material or a fibrous material. The material is preferably a porous one, and the porosity may be unidirectional or multidirectional. The term "unidirectional" as used herein may mean that all fibers or pores are lined up in parallel to the axis of the carrier, and the term "multidirectional" may mean omnidirectional, namely that fibers or pores show no particular orientational tendency with respect to liquid permeation or penetration. Preferred examples of the carrier are polypropylene, polyethylene, polyvinylidene fluoride, ethylene-vinyl acetate copolymers, polyacrylonitrile, polytetrafluoroethylene and like plastics, paper, filter paper, nitrocellulose and other various cellulosic materials. The label for the labeled antibody may be selected from among the labels mentioned hereinabove, and those giving signals which are directly visible by the eye, for example gold colloid, pigment or dye sols, and colored latexes, are used with advantage. The labeled antibody can be applied to the carrier by injecting into the carrier or applying to the surface or layering on the surface using a microsyringe or microinjector, for instance. The technique for antibody immobilization may be selected from among those mentioned hereinabove.

In applying various analytical and assaying method, inclusive of these individual immunological assay methods, to the assay method of the present invention, it is not necessary to select any particular conditions or particular procedure. It is only necessary to construct an assay system relating to the target substance according to the present invention or a substance substantially equivalent in activity thereto while adding ordinary technical considerations of the one skilled in the art to general conditions and procedure for each analytical/assay method.

Epitope mapping can also be made using the anti-cauxin antibody of the present invention, in particular a monoclonal antibody. When antibodies recognizing respective epitopes are used, each of cauxin and related peptide fragments and the like can be detected and/or assayed.

As mentioned hereinabove, the feline nephropathy diagnosing/detecting agent comprising an anti-cauxin antibody obtained as a polyclonal antibody (inclusive of antiserum) or monoclonal antibody can be used in immunohistologically analyzing the cauxin levels using, as samples, cells extracted from tissues such as kidneys. Thus, feline nephropathy can be detected and diagnosed by analyzing the cauxin level in target cells.

Here, the feline nephropathy diagnosing agent may comprise an anti-cauxin antibody as an active ingredient. The term "comprising as an active ingredient" means that the anti-cauxin antibody is contained at a sufficient concentration to detect feline nephropathy. The recognition site of the anti-cauxin antibody is not limited to the epitope but may be at any region of the cauxin protein.

The term "cauxin" as used herein may mean not only cauxin shown under SEQ ID NO: 2 in the sequence listing but also natural mutants of cauxin, mutants derived therefrom by artificial mutation (namely, deletion, addition, modification or insertion, for instance, of one or more amino acid residues) and partial domains or partial peptide fragments.

As typical anti-cauxin antibodies, there may be mentioned antibodies binding to all such cauxin species, antibodies specific to the C-terminal side domain of cauxin or fragment peptides thereof, and antibodies specific to the N-terminal side domain of cauxin or fragment peptides thereof, for instance.

Advantageous for utilization in the cauxin assaying system are such protein assaying systems as immunostaining (METHODS, 24, 289-296 (2001); J. Immunol Methods, 47 (2), 129-144 (1981); ibid., 150 (1-2), 5-21, 23-32 & 151-158 (1992); Cancer J., 7 (1), 24-31 (2001), etc.) and immune electron microscopy (Mol. Biotechnol., 7 (2), 145-151 (1997); J. Electron Microsc. Tech., 19 (1), 57-63 & 64-79 (1991); ibid., 19 (3), 305-315 (1991), etc.) and such expressed gene assaying systems as in situ hybridization in the case of tissue samples, for instance, such protein assaying systems as EIA, RIA, FIA, LIA, western blotting (J. Electron Microsc. (Tokyo), 45 (2), 119-127 (1996); Methods Biochem. Anal., 33, 1-58 (1988); Methods Enzymol., 271, 177-203 (1996); ibid., 305, 333-345 (2000); J. Immunol Methods, 152 (2), 227-236 (1992); ibid., 170 (2), 177-184 (1994); ibid., 195 (1-2), 149-152 (1996); Yoshiyuki Kuchino et al. (ed.), "Idenshi/Tanpakushitsu, Jikken Sosa (Genes/Proteins, Experimental Procedures): Blotting", Kabushiki Kaisha Soft Science, published Nov. 10, 1987, etc.) and such expressed gene assaying systems as northern blotting, dot blot, RNase protection assay, RT-PCR (reverse transcription polymerase chain reaction), Real-Time PCR (Clinical Chemistry, 46: 11, 1738-1743 (2000) for tissue extracts, and such protein assaying systems as EIA, RIA, FIA, LIA, and western blotting for blood, body fluid and like sample. For the anti-cauxin antibody assaying systems, such protein assaying systems as EIA, RIA, FIA, LIA, and western blotting can advantageously be utilized for blood, body fluid and like samples.

In EIA systems, in the case of competitive method, for instance, the anti-cauxin antibody is used as an immobilized antibody and a labeled antigen and an unlabeled antigen (cauxin or a fragment peptide thereof may be mentioned as the antigen) are used and, in the noncompetitive method, for example the sandwich method, an immobilized anti-cauxin antibody or a labeled anti-cauxin antibody can be utilized or the anti-cauxin may be directly labeled or an antibody to the anti-cauxin antibody may be labeled without immobilization or with immobilization. As the sensitivity increasing method, there may be mentioned the utilization, in the combination with a non-enzyme-labeled primary antibody, of a macromolecular polymer and an enzyme and the primary antibody (application of Envision reagent: Enhanced polymer one-step staining (EPOS)) and, in the combination with a non-enzyme-labeled secondary antibody, the combination of an enzyme and an anti-enzyme antibody complex as in the PAP (peroxidase-antiperoxidase) technique, the combination of a biotin-labeled secondary antibody and a biotin-labeled enzyme-avidin complex as in the SABC (avidin-biotinylated peroxidase complex) method, the combination of a biotin-labeled secondary antibody and a biotin-labeled enzyme-streptavidin complex as in the ABC (streptavidin-biotin complex) method or the LSAB (labeled streptavidin-biotin) method, the combination of SABC, a biotin-labeled tyramide and an enzyme-labeled streptavidin as in the CSA (catalyzed signal amplification) method, and the use of a macromolecular polymer labeled with a secondary antibody and an enzyme, among others.

For the particulars of these general technological means, review articles, monographs and so on may be referred to [for example, Hiroshi Irie (ed.), "Radioimmunoassay", Kodansha, published 1974; Hiroshi Irie (ed.), "Radioimmunoassay, Volume Two", Kodansha, published 1979; Eiji Ishikawa et al. (ed.), "Koso Men'eki Sokuteiho (Enzyme Immunoassay)", Igaku Shoin, published 1978; Eiji Ishikawa et al. (ed.), "Koso Men'eki Sokuteiho" (second edition), Igaku Shoin, published 1982; Eiji Ishikawa et al. (ed.), "Koso Men'eki Sokuteiho" (third edition), Igaku Shoin, published 1987; H. V Vunakis et al. (ed.), "Methods in Enzymology", V61. 70 (Immunological Techniques, Part A), Academic Press, New York (1980); J. J. Langone et al. (ed.), "Methods in Enzymology", Vol. 73 (Immunological Techniques, Part B), Academic Press, New York (1981); J. J. Langone et al. (ed.), "Methods in Enzymology", Vol. 74 (Immunological Techniques, Part C), Academic Press, New York (1981); J. J. Langone et al. (ed.), "Methods in Enzymology", Vol. 84 (Immunological Techniques, Part D: Selected Immunoassays), Academic Press, New York (1982); J. J. Langone et al. (ed.), "Methods in Enzymology", Vol. 92 (Immunological Techniques, Part E: Monoclonal Antibodies and General Immunoassay Methods), Academic Press, New York (1983); J. J. Langone et al. (ed.), "Methods in Enzymology", Vol. 121 (Immunological Techniques, Part I: Hybridoma Technology and Monoclonal Antibodies), Academic Press, New York (1986); J. J. Langone et al. (ed.), "Methods in Enzymology", Vol. 178 (Antibodies, Antigens, and Molecular Mimicry), Academic Press, New York (1989); M. Wilchek et al. (ed.), "Methods in Enzymology", Vol. 184 (Avidin-Biotin Technology), Academic Press, New York (1990); J. J. Langone et al. (ed.), "Methods in Enzymology", Vol. 203 (molecular Design and Modeling: Concepts and Applications, Part B: Antibodies and Antigens, Nucleic Acids, Polysaccharides, and Drugs), Academic Press, New York (1991); and references cited therein (the descriptions therein are incorporated herein by reference)].

In another aspect, the present invention provides a feline nephropathy detecting/diagnosing agent characterized by containing a nucleic acid capable of hybridizing with a nucleic acid coding for cauxin or a constituent domain thereof, a feline nephropathy detecting method using the same, and a system to be utilized therefor. As the hybridizing nucleic acid, there may be mentioned, for example, probes and primers. Probes capable of hybridizing with a cauxin gene or a product thereof can be utilized without restriction provided that the intended purpose can be attained. The above nucleic acid can be obtained according to the "gene manipulation technology" mentioned hereinabove. For example, it can be obtained with ease by designing a plurality of primers utilizing the information on the nucleotide base sequence shown under SEQ ID NO: 3 in the sequence listing, synthesizing them and carrying out the PCR (polymerase chain reaction) using them, for instance. The primers can be synthesized by the methods known in the art, typically by the phosphodiester method, phosphotriester method, phosphoamidite method and like methods. For example, they can be synthesized using an automated DNA synthesizer, for example a model 381A DNA synthesizer (Applied Biosystems). PCR is carried out using a cDNA library, together with a sense primer and an antisense primer, whereby cDNA can be amplified. The nucleic acid obtained can be used as a specific hybridization probe. For labeling the probe with a radioisotope, for instance, a commercial labeling kit, such as a random prime DNA labeling kit (Boehringer Mannheim), can be used. The probe DNA can be labeled with $[\alpha\text{-}^{32}P]dCTP$ (Amersham) or the like using a random priming kit (Pharmacia LKB, Uppsala), for instance, whereby a radioactive probe can be obtained. The label of the probe may be any of those known in the relevant field of art and can be adequately selected from among the labels mentioned hereinabove referring to the antibodies.

The hybridization is carried out by transferring the sample holding or carrying the DNA in question to a membrane, such as a nylon filter and, after denaturation, immobilization, washing and/or like treatment, if necessary, reacting the sample transferred to the membrane with the labeled probe DNA fragment (if necessary denatured) in a hybridization buffer. The hybridization treatment is generally carried out at about 35° C. to about 80° C., more preferably at about 50° C. to about 65° C., for about 15 minutes to about 36 hours, more preferably for about 1 hour to about 24 hours. Optimum conditions can properly be selected. Thus, for example, the hybridization treatment is carried out at about 55° C. for about 18 hours. The hybridization buffer can be selected from among those commonly used in the relevant field. Thus, for example, Rapid hybridization buffer (Amersham) can be used. As the denaturation treatment of the membrane after DNA transfer, there may be mentioned the method using an alkaline denaturing solution, and this treatment is preferably followed by treatment with a neutralizing solution of a buffer solution. The immobilization treatment of the membrane is carried out by baking generally at about 40° C. to about 100° C., more preferably at about 70° C. to about 90° C., for about 15 minutes to about 24 hours, more preferably for about 1 hour to about 4 hours. Optimum conditions can properly be selected. Thus, for example, the immobilization is realized by baking the filter at about 80° C. for about 2 hours. The washing treatment of the transferred DNA-carrying membrane can be performed by washing in a washing solution commonly used in the relevant field, for example with 50 mM Tris-HCl buffer, pH 8.0, containing 1 M NaCl, 1 mM EDTA and 0.1% sodium dodecyl sulfate (SDS). The membrane for receiving transferred DNA can be selected from among those generally used in the relevant field, and a nylon filter or the like, for instance, may be mentioned.

The above alkaline denaturing solution, neutralizing solution and buffer solution can be selected respectively from among those generally used in the relevant field. Thus, the alkaline denaturing solution may be, for example, a solution containing 0.5 M NaOH and 1.5 M NaCl, the neutralizing solution may be, for example, 0.5 M Tris-HCl buffer, pH 8.0, containing 1.5 M NaCl, and the buffer solution may be, for example, 2×SSPE (0.36 M NaCl, 20 mM $NaH_2PO_4$ and 2 mM EDTA) or the like. For preventing nonspecific hybridization reactions, the membrane after transfer is preferably subjected to prehybridization treatment according to need prior to the hybridization treatment. This prehybridization treatment can be carried out, for example, by immersing the membrane in a prehybridization solution [50% formamide, 5× Denhardt's solution (0.2% bovine serum albumin, 0.2% polyvinylpyrrolidone), 5×SSPE, 0.1% SDS, 100 µg/ml heat-denatured salmon sperm DNA] or the like, and allowing reactions to proceed at about 35° C. to about 50° C., preferably at about 42° C., for about 4 to about 24 hours, preferably for about 6 to about 8 hours. As for such conditions, the one skilled in the art will be able to selected more preferred conditions after appropriately repeated experiments. The labeled probe DNA fragment to be used for hybridization can be denatured, for example, by heating at about 70° C. to about 100° C., preferably at about 100° C., for about 1 minute to about 60 minutes, preferably for about 5 minutes. The hybridization can be carried out by a per se known method or a modification thereof. The term "stringent conditions" as used herein refers, for example, to such conditions as a sodium concentration of about 15 to about 50 mM, preferably about 19 to about 40 mM, more preferably about 19 to about 20 mM, and a temperature of about 35 to about 85° C., preferably about 50 to about 70° C., more preferably about 60 to about 65° C.

After completion of the hybridization, the filter is sufficiently washed to remove the residual labeled probe other than the labeled probe DNA fragment that has participated in the hybridization reaction. The filter can be washed with a washing solution selected from among those generally used in the relevant field of art and, for example, the filter can be washed with 0.5×SSC (0.15 M NaCl, 15 mM citric acid) solution containing 0.1% SDS, or the like.

The site of hybridization can be detected typically by autoradiography. Any other technique properly selected from among the techniques used in the relevant field may also be used.

Feline nephropathy can be detected by detecting/assaying the cauxin expression gene (including DNA such as cDNA and RNA such as mRNA) by the techniques known for detecting/assaying the expression of a specific gene in the relevant field according to the above-described "gene recombination technology", for example by in situ hybridization, northern blotting, dot blot, RNase protection assay, RT-PCR, Real-Time PCR (Journal of Molecular Endocrinology, 25, 169-193 (2000) and references cited therein), or DNA array analysis (Mark Shena (ed.), "Microarray Biochip Technology", Eaton Publishing (March 2000). The cauxin expression gene assay systems utilizing such techniques, and the reagents, techniques and processes to be utilized therein, for instance, are all included in the feline nephropathy detecting/diagnosing agent, feline nephropathy detecting/diagnosing method and system therefor according to the present invention. The in situ hybridization mentioned above may include non-RI in situ hybridization, for instance, and the direct method and indirect method, for instance, may be included therein. The direct method uses, for example, a detectable molecule (reporter) directly bound to the nucleic acid probe, while the indirect method uses, for example, an antibody to the reporter molecule for attaining signal amplification. The oligonucleotide in the nucleic acid probe contains functional groups (e.g. primary amino group, SH group, etc.) as introduced therein, and a hapten, fluorescent dye or enzyme, for instance, may be bound to such a functional group. As typical examples of the label of the nucleic acid probe, there may be mentioned digoxigenin (DIG), biotin, fluorescein and the like. The label, however, may be selected from among the labels described hereinabove referring to the antibodies, and multiple labeling may also be employed and, further, labeled antibodies may also be utilized. The method of labeling the nucleic acid probe can be properly selected from among the methods known in the relevant field and, thus, for example, there may be mentioned random priming, nick translation, DNA amplification by PCR, labeling/tailing, and in vitro transcription, among others. For observing the treated sample, an appropriate method can be selected from among those methods known in the art. For example, a dark field microscope, phase contrast microscope, reflection contrast microscope, fluorescence microscope, digital imaging microscope, or electron microscope can be used. Further, flow cytometry or the like may also be employed.

In accordance with the present invention, cauxin and the cauxin expression gene can be used as markers for feline nephropathy, and feline nephropathy detecting/diagnosing agents, agents for detection and/or measurement of such a disease, feline nephropathy detecting/diagnosing methods or abnormality detecting and/or measuring methods and, further, reagent kits or systems for such detection and/or measurement can be prepared, established or constructed in various forms utilizing such markers. Furthermore, after treatment of feline nephropathy, they can be utilized also for making a prognosis in the form of disease detecting and/or measuring agents, disease detecting and/or measuring methods and, further, disease detection and/or measuring reagent sets or systems, with feline nephropathy as the target. They can be expected to show good functions and effects in prognosis as well.

The term "marker" as used herein may indicate that it makes it possible to recognize or identify the "feline nephropathy (cat kidney diseases)" or "feline renal abnormality" and, further, may indicate that it can function as a measure of the level of the "disease" in question and the severity of "symptoms". It is to be considered that the term denotes the functions mentioned above according to the presence or absence of the marker and/or the difference in the quantity thereof.

By using a test kit with which feline urinary cauxin can be assayed using an anti-cauxin antibody according to the present invention, the owner can check his/her family cat for health condition in a simple manner without visiting a veterinarian. Further, it becomes possible to find out feline nephropathy before the disease becomes incurable, whereby the life of the family cat can be prolonged. When used by a veterinarian, the kit can give an indicator which can be used in judging the extent of progress of nephropathy and in making a prognosis.

In the present specification and drawings, the terms used are those according to the IUPAC-IUB Commission on Biochemical Nomenclature or conventionally used in the relevant field of art.

EXAMPLES

The following examples illustrate the present invention specifically. These examples are, however, by no means limitative of the scope of the present invention. It is to be understood that various modes of embodiment are possible based on the spirit and ideas disclosed herein. Unless otherwise specified, all the examples were carried out, or can be carried out, using standard techniques which are well known and conventional to those skilled in the art.

In the following examples, unless otherwise pointed out, the specific procedures and treatment conditions employed are as described in the following references: as regards DNA cloning, J. Sambrook, E. F. Fritch & T. Maniatis, "Molecular Cloning", 2nd ed., Cold Spring Harbor Laboratory, Cold Spring Harbor, N.Y. (1989) and D. M. Glover et al. ed., "DNA Cloning", 2nd ed., Vol. 1 to Vol. 4, (The Practical Approach Series), IRL Press, Oxford University Press (1995); as regards PCR, in particular, H. A. Erlich ed., PCR Technology, Stockton Press, 1989; D. M. Glover et al. ed., "DNA Cloning", 2nd ed., Vol. 1, (The Practical Approach Series), IRL Press, Oxford University Press (1995) and M. A. Innis et al. ed., "PCR Protocols", Academic Press, New York (1990). When commercial reagents or kits were used, the protocols attached thereto were referred to and the chemicals or reagents attached thereto were used.

Example 1

(1) Search for and Analysis of a Feline Urinary Protein (a) For analyzing feline urinary proteins, urine samples were collected from adult cats, kittens and cats with nephropathy and subjected to SDS-PAGE under nonreducing conditions.

Thus, a SDS sample buffer was added to 10 µl of urine from each cat (animal of the family Felidae), and the mixture was boiled for 3 minutes and then subjected to SDS-polyacrylamide electrophoresis (SDS-PAGE) under nonreducing conditions using a polyacrylamide gel (12% concentration) according to the method of Laemmli. After electrophoresis, the gel was stained with a Coomassie Brilliant Blue R250 staining solution.

The results are shown in FIG. 1. In the normal healthy adult cat-derived urine samples, a protein having a molecular weight of 70 k was found excreted in high concentrations, irrespective of sex. This protein was not detected in kitten-derived urine samples, while the urinary excretion of the protein was found markedly decreased in cats with nephropathy. This protein was named "cauxin".

(b) For analyzing urinary proteins in animals belong to the family Felidae, urine samples were collected from animals of the subfamily Felinae g house cat group, subfamily Felinae wildcat group, subfamily Pantherinae or subfamily Acinonychinae, and subjected to SDS-PAGE under nonreducing conditions in the same manner as in (a) above.

Figure 2:
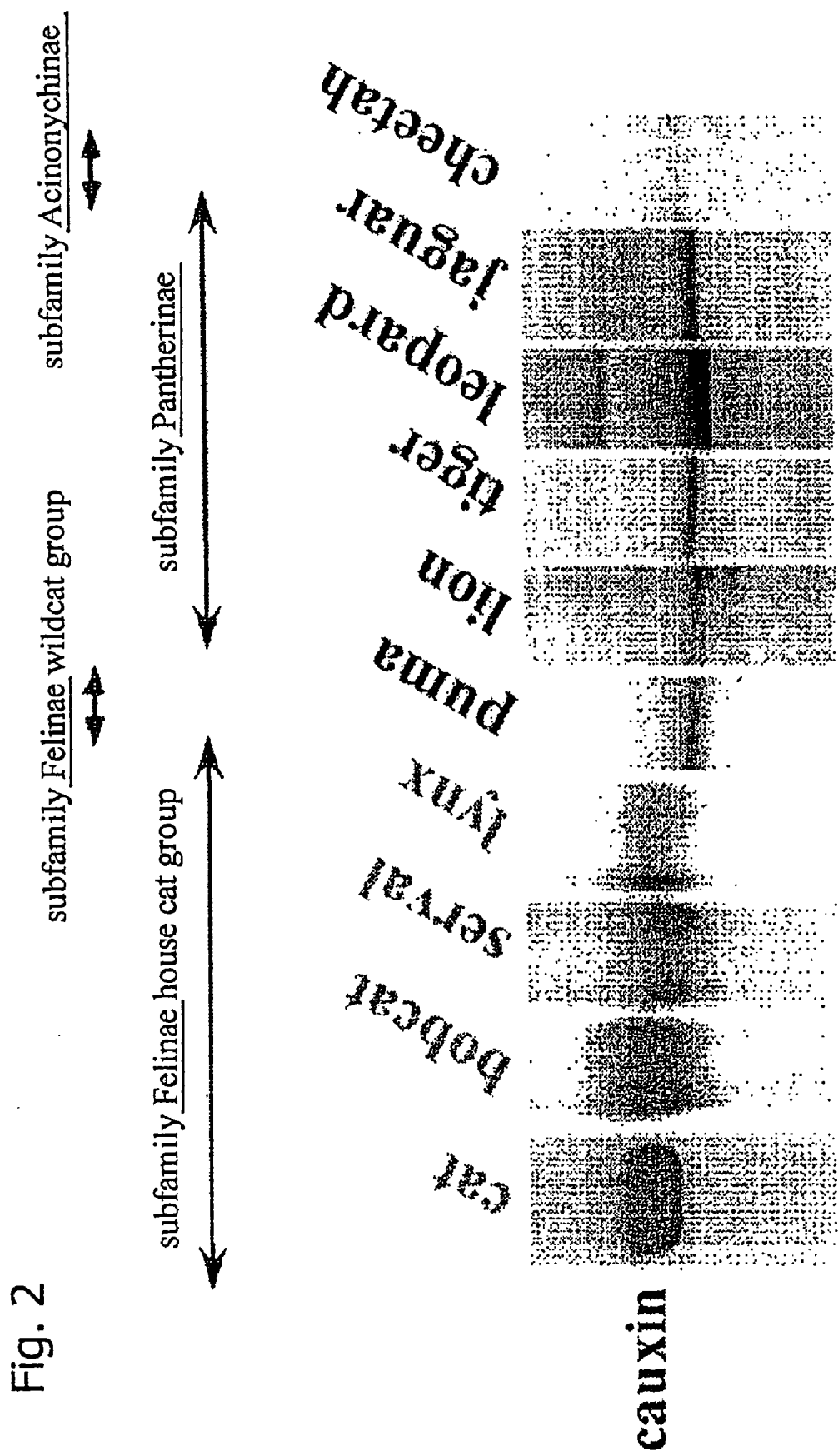
FIG. 2 is a photograph showing the SDS-polyacrylamide gel electrophoresis profiles of proteins in urine samples derived from animals belonging to the family Felidae.

The results are shown in FIG. 2. In bobcat, serval and lynx, a cauxin-like protein of 70 kDa was detected at the same position as the urinary protein (cauxin) identified as described above.

(2) Cloning and Analysis of the Gene Coding for Urinary Protein Cauxin (a) Cloning of Cauxin cDNA Cauxin purified from feline urine was analyzed for the N-terminal amino acid sequence on a protein sequencer (model PPSQ-21, Shimadzu) and, after lysylendopeptidase treatment, the products were analyzed for 7 internal partial amino acid sequences. Based on these results, PCR primers were designed and prepared. RT-PCR was carried out using messenger RNA extracted from the feline kidney as a template. A probe was prepared by labeling the amplified PCR product using the Alkphos direct labeling kit (Amersham Pharmacia Biotech). Then, a feline kidney cDNA library constructed by using the SMART cDNA Library Construction Kit (Clontech) was screened using the above-mentioned probe, and the cauxin cDNA was cloned and analyzed for nucleotide base sequence using a DNA sequencer (model ABI PRISM 310 DNA sequencer, Perkin-Elmer). Based on the results, the full-length amino acid sequence of cauxin was determined.

(b) Analysis of the Cauxin DNA Sequence and Amino Acid Sequence

Figure 3:
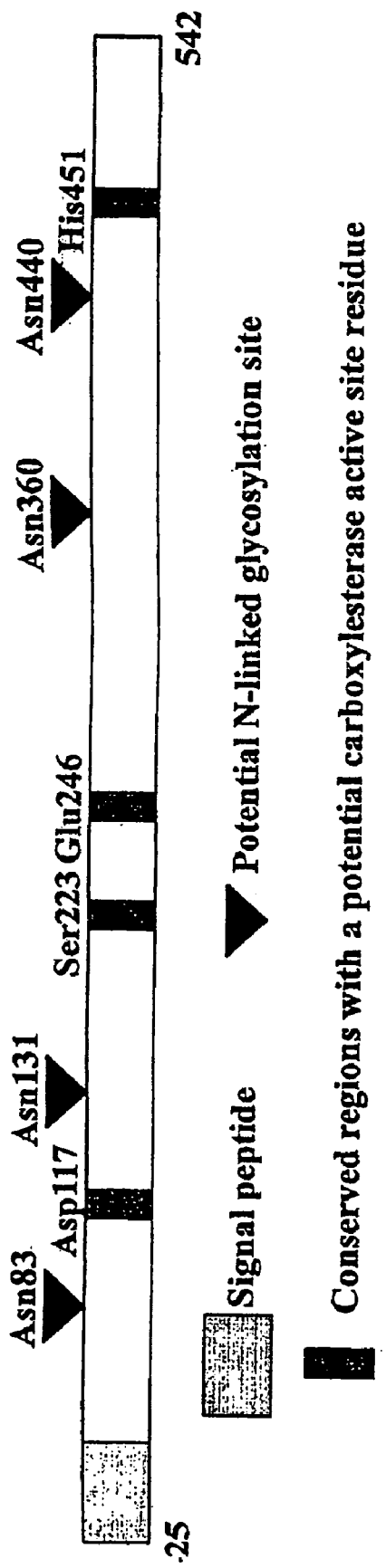
FIG. 3 shows the primary structure of cauxin, in comparison with carboxylesterase.

The nucleotide base sequence of the cauxin DNA cloned as mentioned above was subjected to homology searching using the GenBank™ databases BLASTX and FASTA. Amino acid sequence comparison with carboxylesterase was made using the gene analysis software GENETYX-MAC. The DNA sequence coding for cauxin is shown in the sequence listing under SEQ ID NO: 1, the amino acid sequence of cauxin in the sequence listing under SEQ ID NO: 2, and the sequence of the cloned DNA coding for cauxin in the sequence listing under SEQ ID NO: 3. In FIG. 3, there is shown the primary structure of cauxin, in comparison with carboxylesterase. In FIG. 4, there is shown the C-terminal amino acid sequence alignment of cauxin, in comparison with carboxylesterases obtained from rat kidney, rat liver, swine liver and human liver. The C terminus of cauxin was lacking in endoplasmic reticulum retention signal (HXEL).

Example 2

(1) Production of a Polyclonal Antibody Against the Urinary Protein Cauxin

A cauxin C-terminal amino acid sequence composed of 20 residues was prepared on a peptide synthesizer (model PPSM-8, Shimadzu) and mixed with Freund's complete adjuvant, and the mixture was used to immunize a rabbit. A cauxin-specific antibody was thus prepared.

Figure 5:
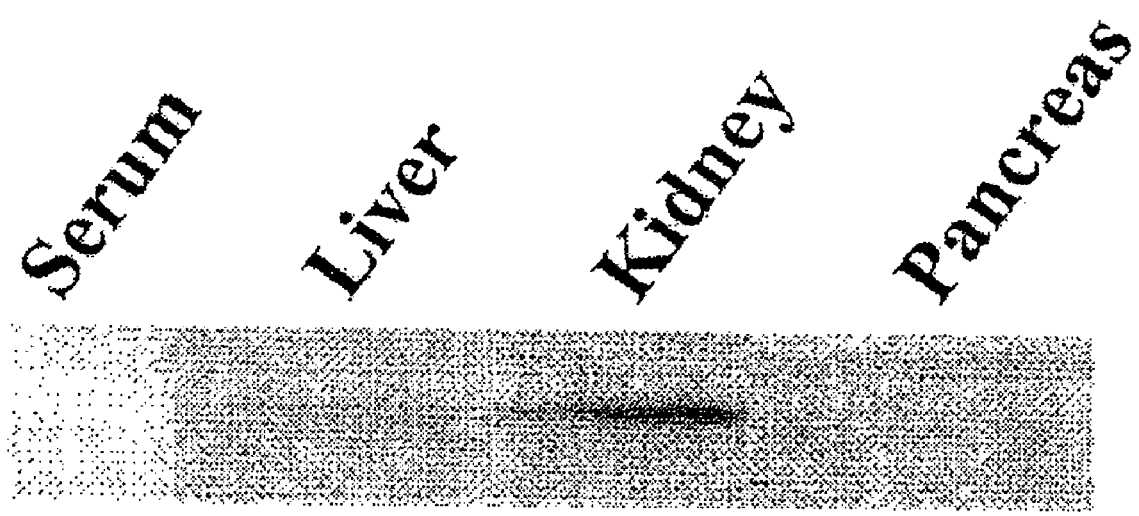
FIG. 5 is a photography showing the patterns of western blotting, following electrophoresis, of protein samples extracted from the cat serum, liver, kidney and pancreas.

(2) Analysis of Tissue Distribution of the Urinary Protein Cauxin (a) Western Blotting Using 1 µg each of the proteins extracted from feline serum, liver, kidney and pancreas, trials for cauxin detection were made with western blotting. The protein (1 µg) extracted feline urine or the protein (5 µg) extracted from each of feline kidney, liver and pancreas was developed by SDS-PAGE, followed by western blotting onto a membrane. The membrane was blocked with 1% polyvinylpyrrolidone in TBS-T (10 mM Tris-HCl, 150 mM NaCl, 0.05% Tween 20, pH 7.4) and then treated with an 8000-fold dilution of cauxin antiserum, a 10000-fold dilution of anti-rabbit IgG-HRP (BioRad) and an ECL kit (Amersham Pharmacia Biotech), followed by detection using an X-ray film (FIG. 5). From FIG. 5, it was confirmed that cauxin is localized in kidneys alone.

(b) Northern Blotting

Figure 6:
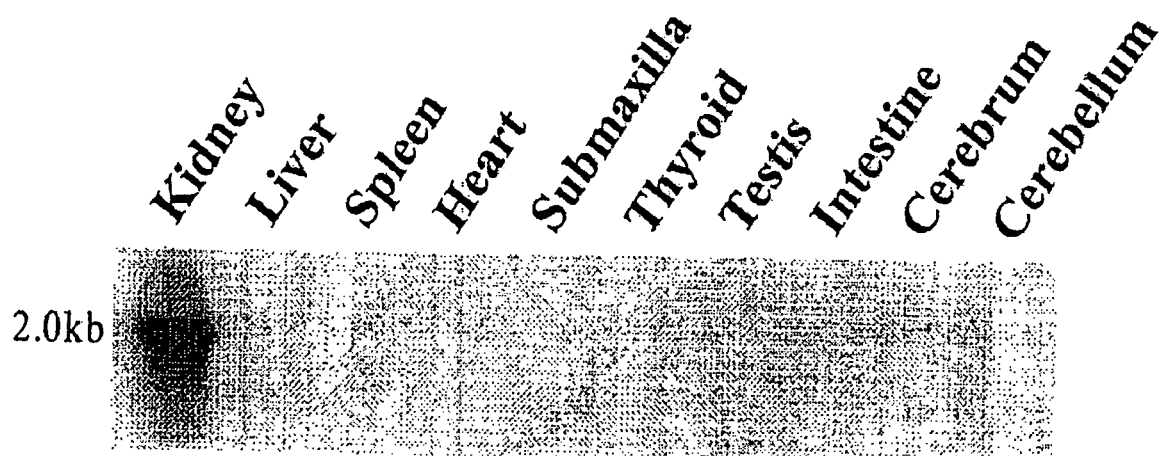
FIG. 6 is a photograph showing the patterns of northern blotting, following electrophoresis, of RNA samples extracted from various cat organs using the cauxin cDNA.

RNA was extracted from each of various cat organs by the AGPC method. Each total RNA (2 µg) was developed on a 1% agarose gel supplemented with paraformaldehyde, followed by northern blotting onto a membrane. After hybridization with the probe, the membrane was washed twice with 1×SSC, 0.1% SDS at 65° C. for 15 minutes and further washed twice with 0.1×SSC, 0.1% SDS at 65° C. for 15 minutes and, after treatment with CDP-star (Amersham Pharmacia Biotech), trials for detection were made using an X-ray film (FIG. 6). From FIG. 6, it was confirmed that cauxin is expressed in kidneys alone. For probe preparation, the cauxin RNA was produced from the full-length cauxin cDNA by in vitro transcription and the RNA was labeled using a DIG labeling kit (Roche Diagnostics).

Example 3

(1) Cauxin Expression in Feline Kidney and Analysis of the Site of Localization (a) In situ Hybridization A feline kidney was fixed with 4% paraformaldehyde, a paraffin-embedded section was then prepared. For probe preparation, the cauxin RNA was produced from the full-length cauxin cDNA by in vitro transcription and the RNA was labeled using a DIG labeling kit (Roche Diagnostics). After hybridization with the probe on the paraffin section, the section was reacted with alkaline phosphatase-conjugated anti-DIG antibodies (Roche Diagnostics) and the cauxin mRNA was detected using Nitro blue tetrazolium/5-bromo-4-chloro-3-indolyl phosphate (Roche Diagnostics).

(b) Immunohistochemistry

After blocking with 10% swine serum (DAKO), the paraffin-embedded section was reacted with a 500-fold dilution of cauxin antiserum overnight at 4° C. After washing three times with Tween-PBS, the section was reacted with anti-rabbit IgG swine serum (DAKO) at 37° C. for 1 hour and further treated with 0.02% diaminobenzidine tetrahydrochloride and 0.005% $H_2O_2$ for detection of cauxin.

(c) Results

Figure 7:
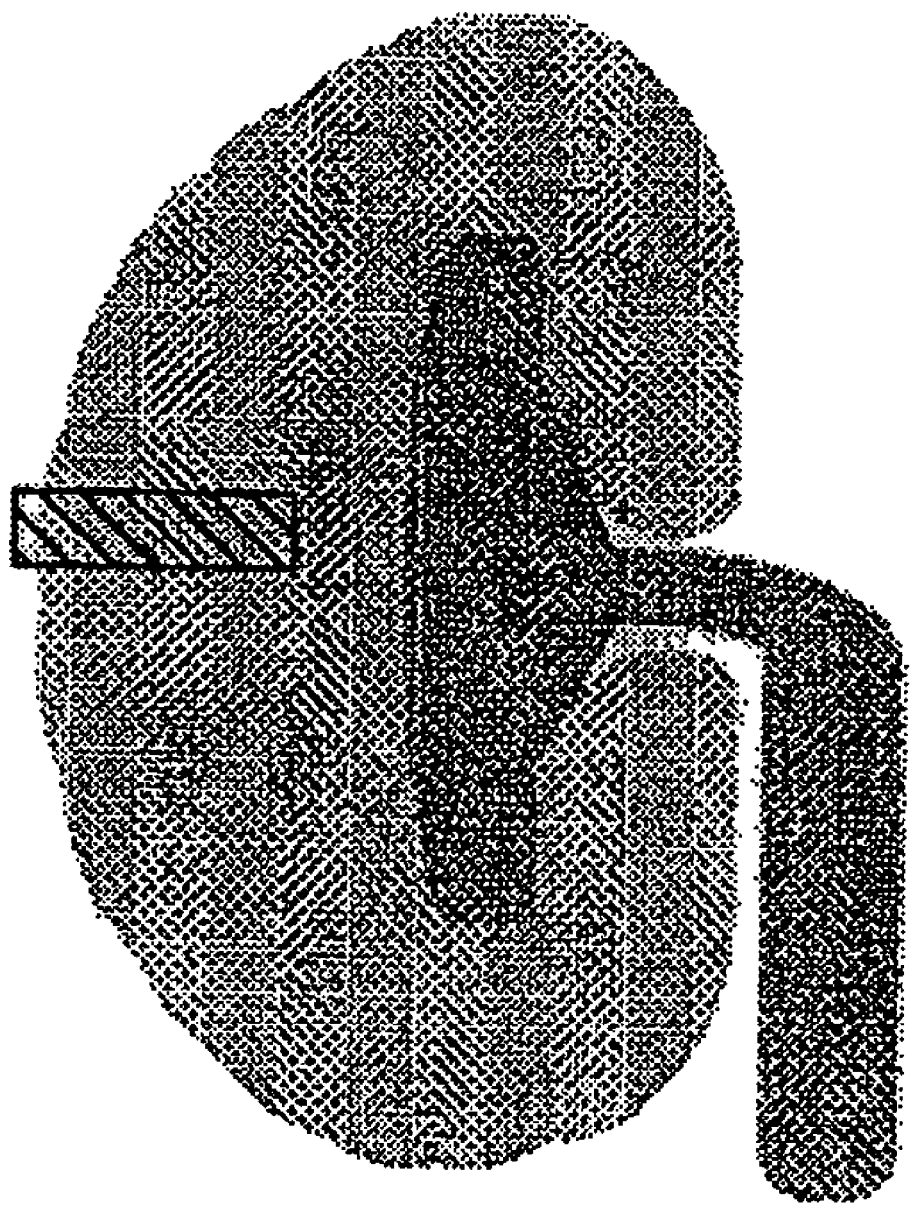
FIG. 7 is a schematic representation of the kidney of an adult cat.
Figure 8:
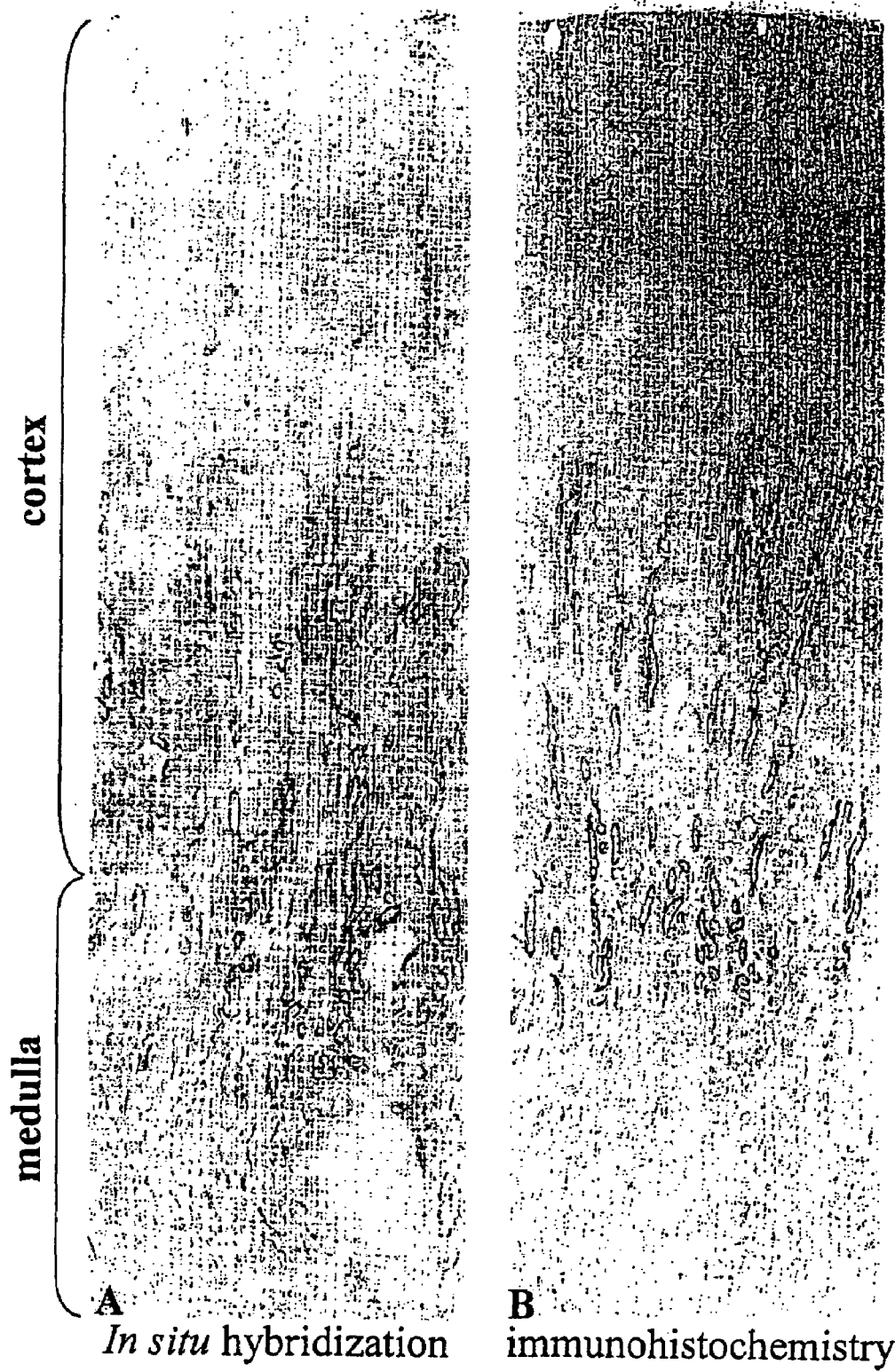
FIG. 8A is a tissue photograph illustrating the in situ hybridization (×50) patterns of the slanting line area shown in FIG. 7.
FIG. 8B is a tissue photograph illustrating the immunohistochemical staining (×50) patterns of the same area.
Figure 10:
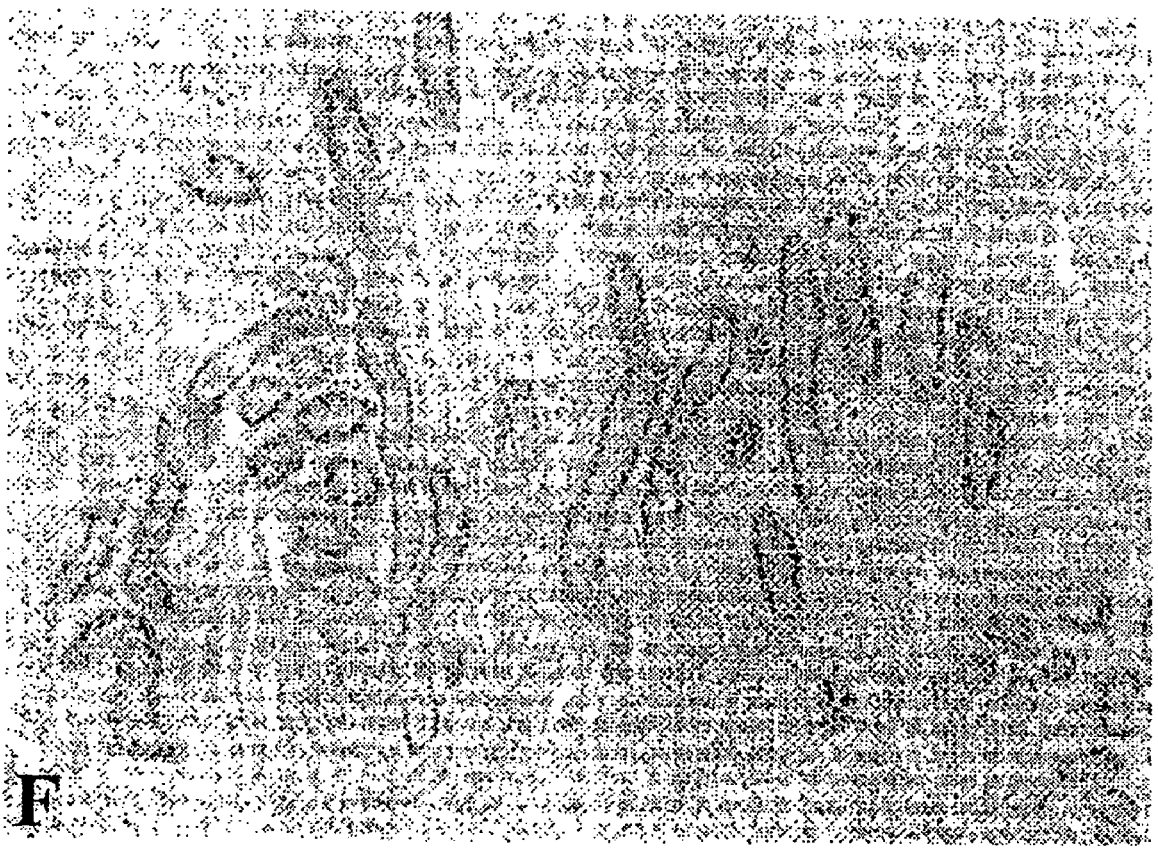
FIG. 10 is a tissue photograph illustrating the immunohistochemical staining (×100) patterns of a corticomedullar transitional zone of an adult cat kidney.
Figure 11:
FIG. 11 is an enlarged tissue photograph (immunohistochemical staining (×200)) of the site shown in FIG. 10.
Figure 12:
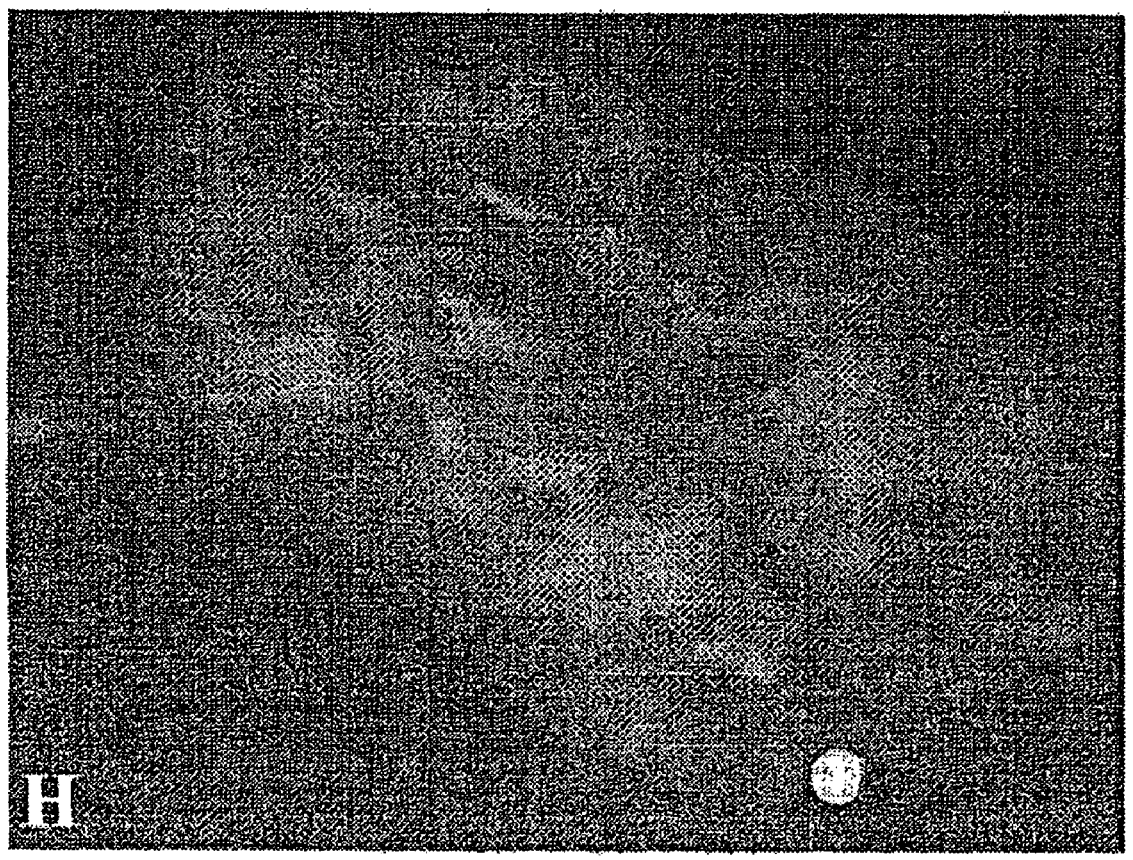
FIG. 12 is a tissue photograph illustrating the results of immunohistochemical staining (×400) using an FITC-labeled antibody.
Figure 13:
FIG. 13 is a tissue photograph illustrating the immune electron microscopy (×60,000) images of the endoplasmic reticulum in tubular epithelial cells.

Cauxin was found localized in distal tubule epithelial cells in the corticomedullar transitional zone in the adult cat kidney. FIG. 7 shows the kidney of an adult cat. FIG. 8A shows the in situ hybridization (×50) patterns of the slanting line area shown in FIG. 7, and FIG. 8B shows the immunohistochemical staining (×50) patterns of the slanting line area shown in FIG. 7. FIG. 9C shows the in situ hybridization (×100) patterns of a corticomedullar transitional zone of an adult cat kidney, FIG. 9D is an enlargement (in situ hybridization (×400)) of the site shown in FIG. 9C, and FIG. 9E shows the in situ hybridization (×200) patterns of a corticomedullar transitional zone of an adult cat kidney. FIG. 10 shows the immunohistochemical staining (×100) patterns of a corticomedullar transitional zone of an adult cat kidney. FIG. 11 is an enlarged tissue photograph (immunohistochemical staining (×200)) of the site shown in FIG. 10. FIG. 12 shows the immunohistochemical staining (×400) patterns when the FITC-labeled antibody was used, and FIG. 13 shows the immune electron microscopy (×60,000) images of the endoplasmic reticulum in tubular epithelial cells.

Example 4

(1) The cauxin levels in each µg of the urinary protein were quantitatively compared in cats at various stages of nephropathy. SDS-PAGE was carried out according to the procedure of Example 1 (1)(a).

Figure 14:
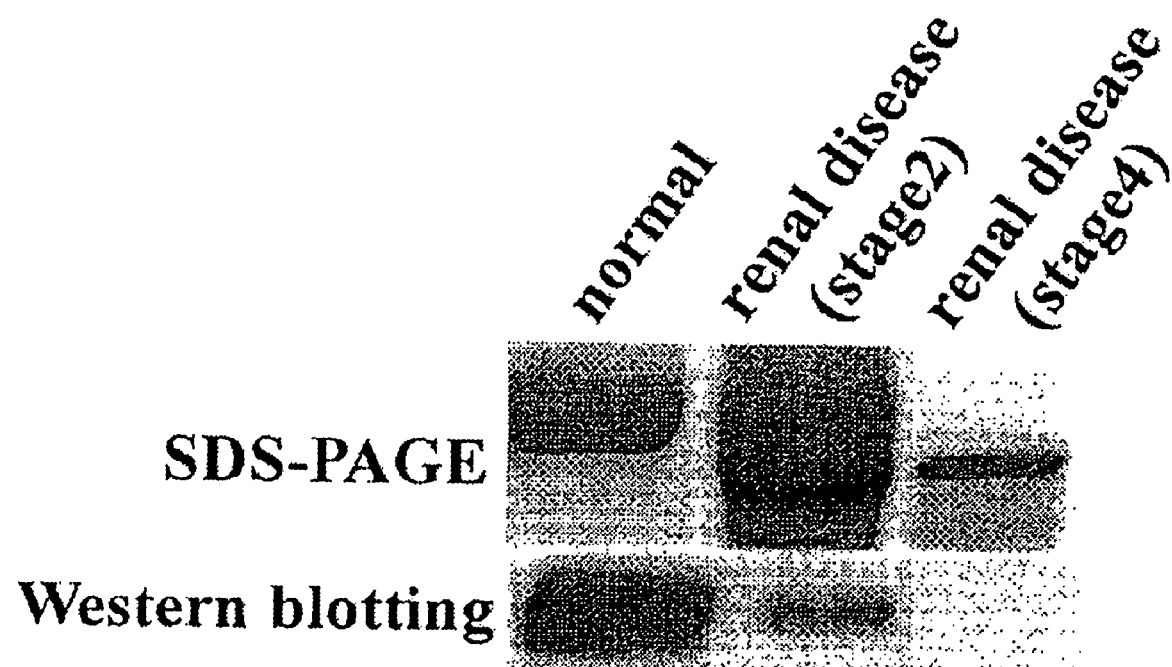
FIG. 14 is a photograph showing the SDS-polyacrylamide electrophoresis profiles of normal cat-derived and nephropathic cat-derived urinary protein samples.

Quantitative western blotting was carried out in the following manner. Thus, 1 µg of the urinary protein derived from a cat with nephropathy was developed by SDS-PAGE and, then, cauxin was detected by western blotting, as described in Example 2 (2)(a). The cauxin levels were compared based on the differences in band density (FIG. 14). From FIG. 14, it was revealed that the urinary excretion of cauxin and the cauxin level in urine per total urinary protein markedly decrease with the advancement in disease stage of nephropathy.

(2) Staining of a Tissue Derived from a Cat with Interstitial Nephritis

Figure 15:
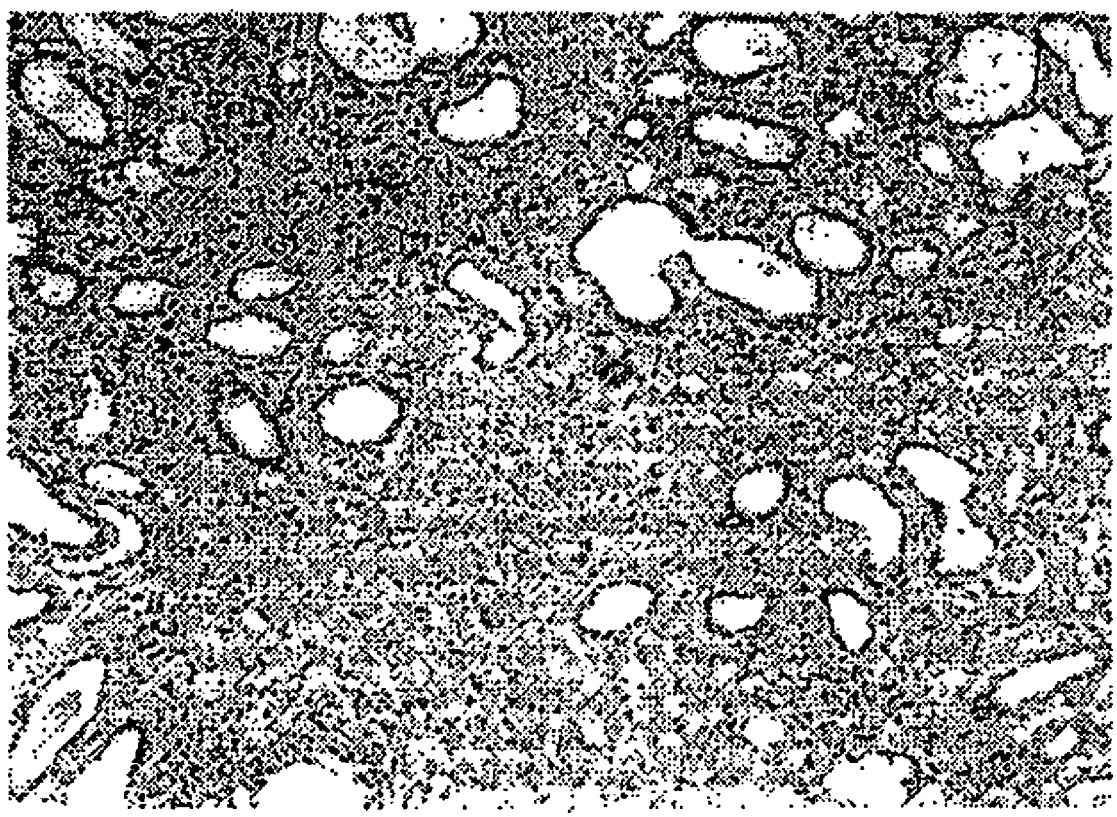
FIG. 15 is a tissue photograph showing the staining patterns of a tissue derived from a cat with interstitial nephritis.
Figure 16:
FIG. 16 is a tissue photograph showing the immunostaining patterns for counting cauxin-producing cells in a corticomedullar transitional zone of a normal (healthy) cat.
Figure 17:
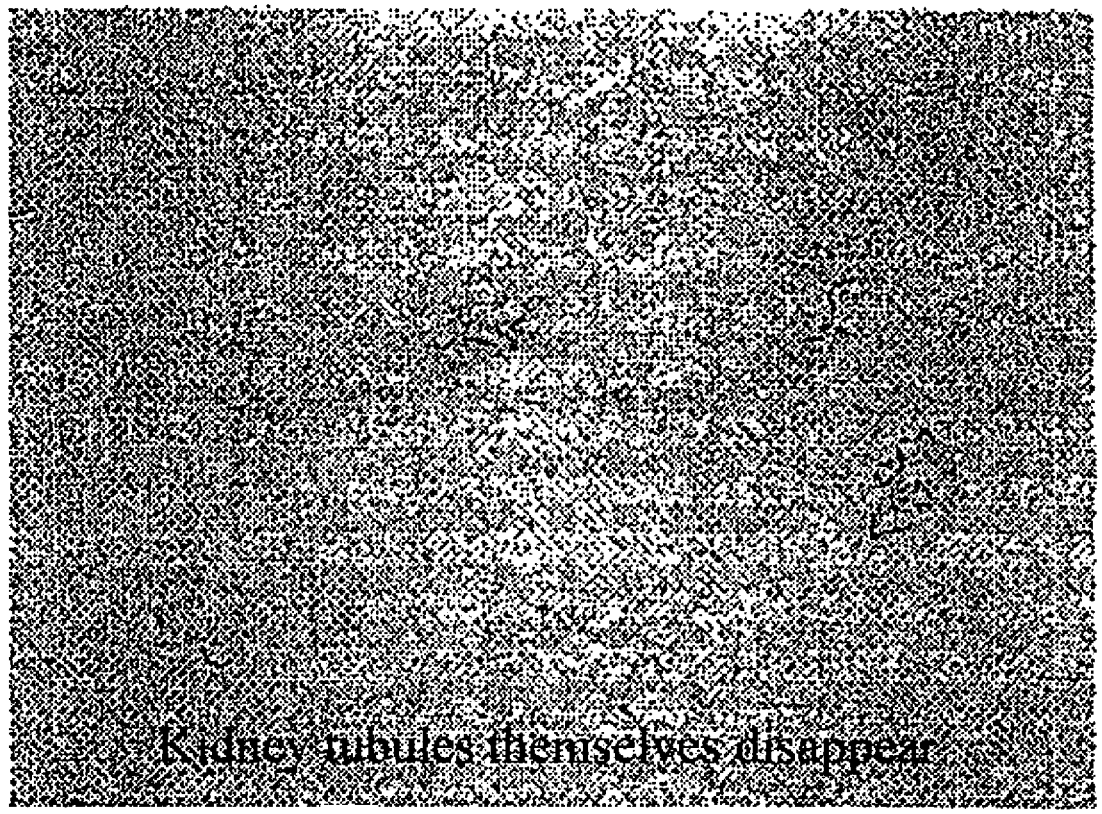
FIG. 17 is a tissue photograph showing the immunostaining patterns for counting cauxin-producing cells in a corticomedullar transitional zone of a cat with nephropathy.

A kidney of a cat which had died of nephropathy was fixed with 4% paraformaldehyde and, then, a paraffin-embedded section was prepared and stained with hematoxylin and eosin. It was observed that kidney tubules had been broken and become hollow and other cells had entered the cavities (FIG. 15). Further, immunostaining comparison was made in the number of cauxin-producing cells in the corticomedullar transitional zone between a healthy cat and a cat with nephropathy (FIG. 16 and FIG. 17). The immunostaining was carried out according to the method described in Example 3 (1)(b). In the cat at the last stage of nephropathy, the number of cauxin-producing cells was found markedly decreased.

Example 5

Gold Colloid Immunochromatographic Test Kit (1) A gold colloid-labeled antibody is prepared by conjugating an appropriate amount of the anti-cauxin antibody to a gold colloid solution. The preparation of the gold colloid solution and the labeling of the anti-cauxin antibody were carried out in the conventional manner.

(2) A oblong strip-like filer paper is prepared which has a sample padding site for dropping a liquid sample, a gold colloid phase where the gold colloid-labeled antibody is positioned, a trapping site with the anti-cauxin antibody immobilized thereon, and an absorbent pad for absorbing the reaction mixture, with the four elements being disposed in line.

(3) When a cauxin-containing feline urine sample is dropped onto the sample pad, the sample migrates to the gold colloid phase owing to the chromatographic phenomenon and urinary cauxin is bound to the gold colloid-labeled antibody;

(4) The gold colloid with cauxin bound to the surface thereof then further diffuses to the trapping site where the gold colloid is immobilized by the antibody on the trapping site; and (5) Upon flocculation of the gold colloid on the trapping site, the site is found colored red purple. If cauxin is absent in the urine sample, the gold colloid passes through the trapping site and migrates to the absorbent pad, so that no coloration can be observed. When the urinary concentration of cauxin is high, the amount of the gold colloid flocculate increases, hence the coloration becomes intense (or the colored area extends). Thus, quantitative assaying becomes possible.

The invention claimed is:

1. An isolated nucleic acid which has a nucleotide base sequence coding for a cauxin protein of SEQ ID NO: 2.

2. The isolated nucleic acid according to claim 1 which is characterized by
   (a) having the nucleotide base sequence shown under SEQ ID NO: 1 in the sequence listing,
   (b) having the nucleotide base sequence shown under SEQ ID NO: 3 in the sequence listing,
   (c) having at least the sequence from the 250th nucleotide base to the 1803rd nucleotide base out of the nucleotide base sequence shown under SEQ ID NO: 3 in the sequence listing, or
   (d) being capable of hybridizing with a sequence having any of the sequences defined above from (a) to (c), under the following wash conditions of 1.0×SSC, 0.1% SDS at 65° C. for 15 minutes.

3. A vector which contains the nucleic acid according to claim 1.

4. A transformant in which the nucleic acid according to claim 1 is harbored.

5. A method of making a cauxin protein comprising cultivating the transformant of claim 4 in culture and recovering the cauxin protein from the culture.

6. The isolated nucleic acid according to claim 1 which is characterized by its serving as a marker for diagnosing feline nephropathy.

7. The isolated nucleic acid according to claim 1 which encodes for an amino acid sequence which is characterized by
   (a) having at least the sequence $Asp^{26}$ to $Pro^{542}$ out of the amino acid sequence shown under SEQ ID NO: 2 in the sequence listing, or
   (b) having the amino acid sequence shown under SEQ ID NO: 2 in the sequence listing.

* * * * *